(12) United States Patent
Kim et al.

(10) Patent No.: US 9,962,082 B2
(45) Date of Patent: May 8, 2018

(54) METHOD FOR MEASURING BIOMETRIC INFORMATION AND ELECTRONIC DEVICE PERFORMING THE SAME

(71) Applicant: Samsung Electronics Co., Ltd., Suwon-si, Gyeonggi-do (KR)

(72) Inventors: Jin Kim, Suwon-si (KR); Hyung Rock Jung, Seoul (KR); Hye Jung Seo, Hwaseong-si (KR); Cheol Ho Cheong, Seoul (KR); Jae Woong Chun, Suwon-si (KR); Won Suk Choi, Seoul (KR); Chang Ryong Heo, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days. days.

(21) Appl. No.: 15/185,674

(22) Filed: Jun. 17, 2016

(65) Prior Publication Data

US 2016/0367138 A1 Dec. 22, 2016

(30) Foreign Application Priority Data

Jun. 19, 2015 (KR) .................. 10-2015-0087739

(51) Int. Cl.
*G08C 19/22* (2006.01)
*H04Q 9/00* (2006.01)
(Continued)

(52) U.S. Cl.
CPC .......... *A61B 5/0006* (2013.01); *A61B 5/002* (2013.01); *A61B 5/0004* (2013.01);
(Continued)

(58) Field of Classification Search
CPC ..... A61B 5/0022; A61B 5/0006; A61B 5/742; A61B 5/0008; A61B 5/0004;
(Continued)

(56) References Cited

U.S. PATENT DOCUMENTS 9,175,328 B2    11/2015   Cho et al.
2004/0066898 A1   4/2004   Schick et al.
(Continued)

FOREIGN PATENT DOCUMENTS

EP         2 716 213 A1    4/2014
KR   10-2013-0111713 A    10/2013
(Continued)

*Primary Examiner* — Tanmay Shah
(74) *Attorney, Agent, or Firm* — Jefferson IP Law, LLP

(57) ABSTRACT

An electronic device is provided. The electronic device includes a sensor related to measurement of biometric information, at least one module that performs a specific function, a memory that stores an instruction related to operations of the sensor and the module, and at least one processor electrically connected to the sensor, the at least one module, and the memory to execute the instruction. When acquiring an event related to initiation of the measurement of the biometric information, the processor may deactivate at least one function of a module, or execute an instruction such that the deactivation state is maintained or the operating mode (for example, a low power mode) of the electronic device is changed.

18 Claims, 14 Drawing Sheets

(51) Int. Cl.
*A61B 5/00* (2006.01)
*A61B 5/024* (2006.01)
*A61B 5/145* (2006.01)
*G01N 33/487* (2006.01)
*G06F 19/00* (2018.01)
*A61B 5/1486* (2006.01)

(52) U.S. Cl.
CPC .......... *A61B 5/0008* (2013.01); *A61B 5/0022* (2013.01); *A61B 5/02438* (2013.01); *A61B 5/14532* (2013.01); *A61B 5/14865* (2013.01); *A61B 5/681* (2013.01); *A61B 5/6803* (2013.01); *A61B 5/6898* (2013.01); *A61B 5/7203* (2013.01); *A61B 5/742* (2013.01); *G01N 33/48785* (2013.01); *G06F 19/34* (2013.01); *A61B 2560/0209* (2013.01); *A61B 2562/0295* (2013.01)

(58) Field of Classification Search
CPC . A61B 5/14865; A61B 5/002; A61B 5/14532; A61B 5/6803
USPC ..................................... 340/870.07
See application file for complete search history.

(56) References Cited

U.S. PATENT DOCUMENTS

| | | |
|---|---|---|
| 2006/0193436 A1 | 8/2006 | Schick et al. |
| 2006/0229520 A1 | 10/2006 | Yamashita et al. |
| 2007/0191719 A1 | 8/2007 | Yamashita et al. |
| 2009/0295566 A1* | 12/2009 | Weintraub ........... G08B 21/088 340/539.11 |
| 2012/0095312 A1* | 4/2012 | Ramey .................. A61B 5/002 600/365 |
| 2012/0150047 A1 | 6/2012 | Terumoto et al. |
| 2013/0261405 A1 | 10/2013 | Lee et al. |
| 2014/0010378 A1* | 1/2014 | Voix ..................... H04R 1/1083 381/57 |
| 2014/0102896 A1 | 4/2014 | Cho et al. |
| 2014/0206969 A1 | 7/2014 | Lee et al. |

FOREIGN PATENT DOCUMENTS

| | | |
|---|---|---|
| KR | 10-2014-0013108 A | 2/2014 |
| KR | 10-2014-0046913 A | 4/2014 |
| KR | 10-2014-0094931 A | 7/2014 |
| WO | 2004/032481 A2 | 4/2004 |

* cited by examiner

METHOD FOR MEASURING BIOMETRIC INFORMATION AND ELECTRONIC DEVICE PERFORMING THE SAME

CROSS-REFERENCE TO RELATED APPLICATION(S)

This application claims the benefit under 35 U.S.C. § 119(a) of a Korean patent application filed on Jun. 19, 2015 in the Korean Intellectual Property Office and assigned Serial number 10-2015-0087739, the entire disclosure of which is hereby incorporated by reference.

TECHNICAL FIELD

The present disclosure relates to a method for measuring biometric information related to a control of a module that may influence the measurement preciseness of biometric information, and an electronic device that performs the method.

BACKGROUND

In recent years, due to various factors, chronic diseases such as cardiovascular diseases, high blood pressure, and diabetes have been increasing. The chronic disease patients need to be treated by doctors, but should manage their own health states by periodically measuring biometric information (for example, a blood pressure, blood glucose, a heart rate (or heart pulsations), and an electrocardiogram (ECG)) by themselves.

For example, the diabetes patients need to measure blood glucose by about 6 times per day, to maintain and adjust a suitable glucose value in everyday life. Further, for example, the patients that suffer from the heart diseases such as myocardial infarction, angina pectoris, and arrhythmia need to regularly measure an ECG to identify whether the heart pulsations of the heart are normal or not.

The medical device manufacturers have developed domestic medical instruments (for example, a hemadynamometer, a blood glucose monitor, an insulin pump, a heartbeat meter, and an ECG monitor) for measuring biometric information such as blood glucose or an ECG in very various ways. Further, the standardization of the medical instruments and medical services also are being actively performed together.

Due to the development of mobile communication technologies, the portable electronic devices, such as smartphones, tablet personal computers (PCs), and wearable devices, employ some or all of the functions of other dedicated devices (for example, a medical instrument), pursuing high functionality.

When a function of a medical instrument is mounted on the portable electronic device, the portable electronic device may employ various biometric sensors.

For example, the biometric sensor may correspond to a glucose sensor that uses an electrochemical principle or an optical principle. The glucose sensor may measure blood glucose based on an electrochemical reaction or an optical reaction between blood provided in the glucose sensor and an element of the glucose sensor.

When it comes to a glucose sensor that uses an electrochemical principle, a glucose sensor strip containing blood of the user may be connected to the glucose sensor through a connector. An enzyme electrode of the glucose sensor may generate a current through an electrochemical reaction between the blood and the blood glucose of the user. The glucose sensor may detect a change in a fine current or voltage that is obtained from the electrochemical reaction, and may measure blood glucose by amplifying the fine current or voltage.

Further, for example, the biometric sensor may correspond to an ECG sensor. The heart acts as a pump that circulates blood throughout the whole human body, and is repeatedly contracted and expanded regularly. The heart may generate a fine amount of electricity whenever it is repeatedly contracted and released. Due to the weak electricity, a current flows through the human body and an electric potential is generated on a surface of the human body due to the current.

The ECG sensor may detect and amplify a fine electrical change due to the pumping operation of the heart and may output the amplified electrical change in the form of a figure. For example, the ECG sensor may detect electric potentials on the surfaces of the human body through a plurality of electrodes attached to a portion of the human body, and may output the electric potentials in a curve.

Further, for example, the biometric sensor may correspond to a photoplethysmogram (PPG) sensor. The PPG sensor may irradiate light of a specific intensity to a part (for example, a finger or a wrist) of the human body through a light emitting module. The PPG sensor may measure pulse waves by detecting the intensity of the received light that is changed by contraction and expansion of a blood vein, a change in the color of the blood, or the like, through a light receiving module.

The above-mentioned biometric sensors measure biometric information by using a very weak electrical signal or optical signal in common. Accordingly, the biometric sensor can guarantee the preciseness and reliability of measurement, only if receiving a sufficient amount of computing resources for operating the biometric sensor while receiving electric power very precisely and stably.

Further, the biometric information may be vulnerable to external noise because it is calculated based on very weak electrical/optical signals. Accordingly, the preciseness and reliability of measurement of biometric information can be improved by effectively interrupting external noise.

For example, the glucose sensor should precisely and stably receive electric power from a power source to improve the preciseness of measurement. Further, in the case of the ECG sensor, electrical noise by external stimuli also should be maximally interrupted to obtain an accurate ECG result. In the case of the PPG sensor, the light emitting module and the light receiving module should receive electric power precisely and stably to measure pulse waves of high reliability, and in particular, the light receiving module should effectively interrupt optical noise from the outside.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages, and to provide at least the advantages described below. Accordingly, an aspect of the present disclosure is to provide a method for measuring biometric information by which a module of various modules included in an electronic device is deactivated such that a biometric sensor included in the electronic device measures the corresponding biometric information with a high preciseness and reliability, and an electronic device that performs the method.

In accordance with an aspect of the present disclosure, an electronic device is provided. The electronic device includes a sensor that measures biometric information, at least one module, a memory that stores an instruction related to operations of the sensor and the at least one module, and at least one processor electrically that is connected to the sensor, the at least one module and the memory, and executes the instruction. If an event related to initiation of the measurement of the biometric information is acquired, the at least one processor deactivates at least one function of a specific module of the at least one module, or maintain the deactivation state or the operating mode (for example, a low power mode) of the specific module.

In accordance with another aspect of the present disclosure, a method for measuring biometric information in an electronic device including one or more modules is provided. The method includes receiving an event related to initiation of a measurement of biometric information, and deactivating at least one function of a module of the one or more modules.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
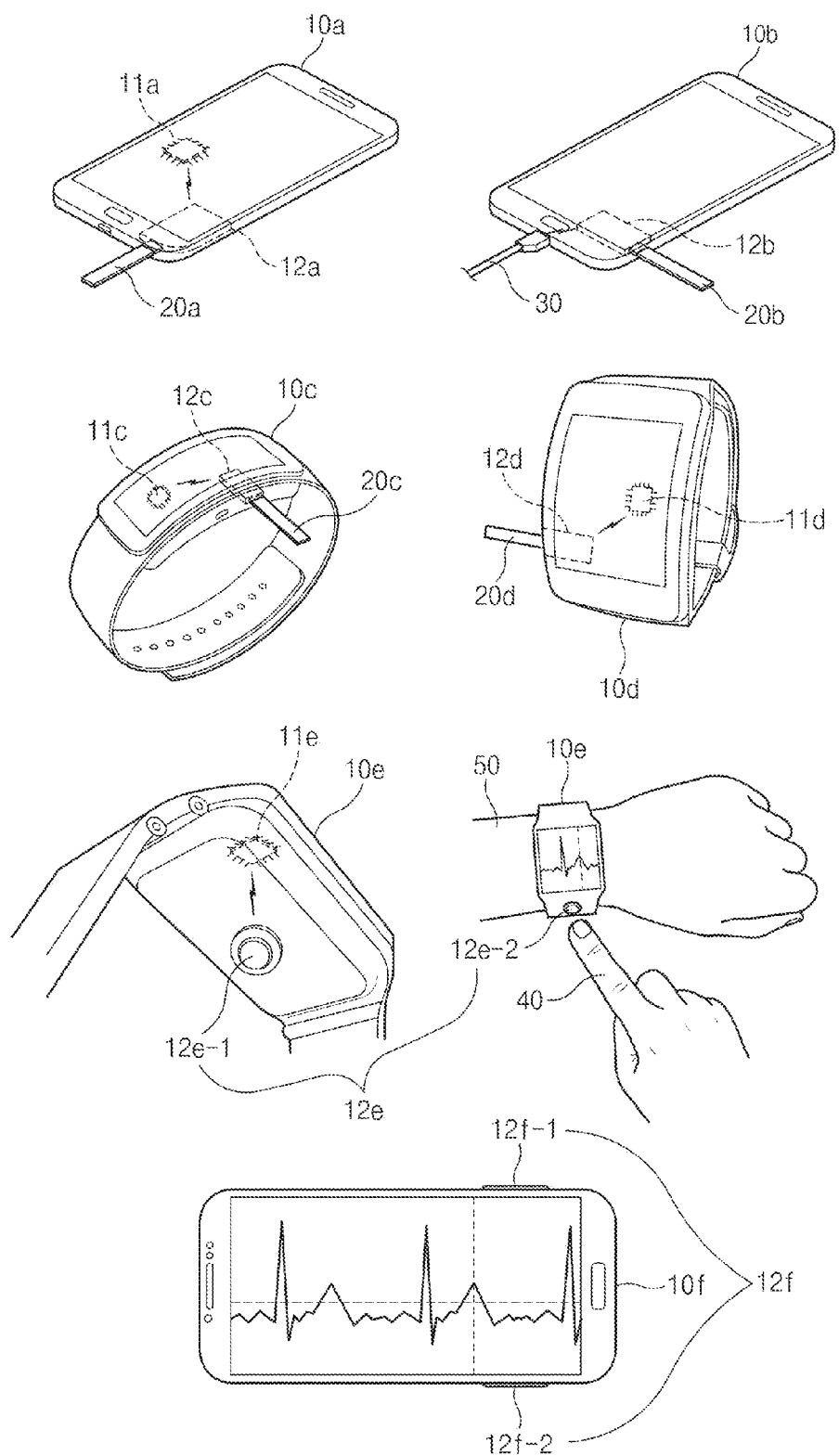
FIG. 1 is views of an electronic device that performs a method for measuring biometric information according to an embodiment of the present disclosure.

The following description with reference to the accompanying drawings is provided to assist in a comprehensive understanding of various embodiments of the present disclosure as defined by the claims and their equivalents. It includes various specific details to assist in that understanding, but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a", "an", and "the", include plural referents unless the context clearly dictates otherwise. Thus, for example, reference to "a component surface" includes reference to one or more of such surfaces.

In the disclosure disclosed herein, the expressions "have", "may have", "include" and "comprise", or "may include" and "may comprise" used herein indicate existence of corresponding features (for example, elements such as numeric values, functions, operations, or components) but do not exclude presence of additional features.

In the disclosure disclosed herein, the expressions "A or B", "at least one of A or/and B", or "one or more of A or/and B", and the like used herein may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The terms, such as "first", "second", and the like used herein may refer to various elements of various embodiments of the present disclosure, but do not limit the elements. For example, such terms are used only to distinguish an element from another element and do not limit the order and/or priority of the elements. For example, a first user device and a second user device may represent different user devices irrespective of sequence or importance. For example, without departing the scope of the present disclosure, a first element may be referred to as a second element, and similarly, a second element may be referred to as a first element.

It will be understood that when an element (for example, a first element) is referred to as being "(operatively or communicatively) coupled with/to" or "connected to" another element (for example, a second element), it can be directly coupled with/to or connected to the other element or an intervening element (for example, a third element) may be present. In contrast, when an element (for example, a first element) is referred to as being "directly coupled with/to" or "directly connected to" another element (for example, a second element), it should be understood that there are no intervening elements (for example, a third element).

According to the situation, the expression "configured to" used herein may be used as, for example, the expression "suitable for", "having the capacity to", "designed to", "adapted to", "made to", or "capable of". The term "configured to (or set to)" must not mean only "specifically designed to" in hardware. Instead, the expression "a device configured to" may mean that the device is "capable of" operating together with another device or other components. Central processing unit (CPU), for example, a "processor configured to (or set to) perform A, B, and C" may mean a dedicated processor (for example, an embedded processor) for performing a corresponding operation or a generic-purpose processor (for example, a CPU or an application processor (AP)) which may perform corresponding operations by executing one or more software programs which are stored in a memory device.

Terms used in this specification are used to describe specified embodiments of the present disclosure and are not intended to limit the scope of the present disclosure. The terms of a singular form may include plural forms unless otherwise specified. Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal detect unless expressly so defined herein in various embodiments of the present disclosure. In some cases, even if terms are terms which are defined in the specification, they may not be interpreted to exclude embodiments of the present disclosure.

An electronic device according to various embodiments of the present disclosure may include at least one of smart-phones, tablet personal computers (PCs), mobile phones, video telephones, electronic book readers, desktop PCs, laptop PCs, netbook computers, workstations, servers, personal digital assistants (PDAs), portable multimedia players (PMPs), Moving Picture Experts Group phase 1 or phase 2 (MPEG-1 or MPEG-2) audio layer 3 (MP3) players, mobile medical devices, cameras, and wearable devices. According to various embodiments of the present disclosure, the wearable devices may include accessories (for example, watches, rings, bracelets, ankle bracelets, glasses, contact lenses, or head-mounted devices (HMDs)), cloth-integrated types (for example, electronic clothes), body-attached types (for example, skin pads or tattoos), or implantable types (for example, implantable circuits).

In some embodiments of the present disclosure, the electronic device may be one of home appliances. The home appliances may include, for example, at least one of a digital video disc (DVD) player, an audio player, a refrigerator, an air conditioner, a cleaner, an oven, a microwave oven, a washing machine, an air cleaner, a set-top box, a home automation control panel, a security control panel, a TV box (for example, Samsung HomeSync™, Apple TV™, or Google TV™), a game console (for example, Xbox™ or Play Station™), an electronic dictionary, an electronic key, a camcorder, or an electronic panel.

In another embodiment of the present disclosure, the electronic device may include at least one of various medical devices (for example, various portable medical measurement devices (a blood glucose meter, a heart rate measuring device, a blood pressure measuring device, and a body temperature measuring device), a magnetic resonance angiography (MRA) device, a magnetic resonance imaging (MRI) device, a computed tomography (CT) device, a photographing device, and an ultrasonic device), a navigation system, a global navigation satellite system (GNSS), an event data recorder (EDR), a flight data recorder (FDR), a vehicular infotainment device, electronic devices for vessels (for example, a navigation device for vessels and a gyro compass), avionics, a security device, a vehicular head unit, an industrial or home robot, an automatic teller's machine (ATM) of a financial company, a point of sales (POS) of a store, or an internet of things (for example, a bulb, various sensors, an electricity or gas meter, a spring cooler device, a fire alarm device, a thermostat, an electric pole, a toaster, a sporting apparatus, a hot water tank, a heater, and a boiler).

According to some embodiments of the present disclosure, the electronic device may include at least one of a furniture or a part of a building/structure, an electronic board, an electronic signature receiving device, a projector, or various measurement devices (for example, a water service, electricity, gas, or electric wave measuring device). In various embodiments of the present disclosure, the electronic device may be one or a combination of the aforementioned devices. The electronic device according to some embodiments of the present disclosure may be a flexible electronic device. Further, the electronic device according to an embodiment of the present disclosure is not limited to the aforementioned devices, but may include new electronic devices produced due to the development of technologies.

Hereinafter, electronic devices according to an embodiment of the present disclosure will be described with reference to the accompanying drawings. The term "user" used herein may refer to a person who uses an electronic device or may refer to a device (for example, an artificial electronic device) that uses an electronic device.

FIG. 1 is views of an electronic device that performs a method for measuring biometric information according to an embodiment of the present disclosure.

Referring to FIG. 1, smartphones 10a and 10b and smartwatches 10c and 10d receive a biometric material and measure biometric information. The smartphones 10a and 10b and the smartwatches 10c and 10d measure biometric information by analyzing the provided biometric material.

For example, the smartphone 10a may include a module 11a that receives electric power from an embedded battery or an external power supply device and performs a predetermined function, and a biometric sensor 12a that measures biometric information. A medium 20a (for example, a glucose sensor strip) containing a biometric material (for example, blood or a deoxyribonucleic acid (DNA)) may be inserted into the biometric sensor 12a. To achieve this, the biometric sensor 12a may include a medium insertion structure.

The smartphone 10b may include a biometric sensor 12b in which a medium 20b containing a biometric material is inserted. The smartphone 10b may receive electric power of a high current from an external device or perform high-speed data communications, through a connection cable 30 (for example, a universal serial bus (USB) cable).

The biometric information may be measured by a wearable device. For example, like the aforementioned smartphones 10a and 10b, the smartwatches 10c and 10d may include a module 11c and 11d that receives electric power from an embedded battery or an external power supply and performs a function, and a biometric sensor 12c and 12d, in which a medium 20c and 20d containing a biometric material is inserted, respectively.

Further, a smartwatch 10e and a smartphone 10f according to an embodiment may be connected to a measurement target (for example, at least a part of the human body) of biometric information to measure biometric information. The smartwatch 10e and the smartphone 10f may apply a specific signal to the human body, and may measure biometric information by amplifying a minute change of a parameter (for example, a voltage, a current, an amount of light, or an electromagnetic field) that is measured in response to the applied signal.

For example, the smartwatch 10e may include a module 11e that performs a function, and a biometric sensor 12e that includes a first electrode 12e-1 and a second electrode 12e-2. For example, the first electrode 12e-1 may correspond to a reference electrode of an electrocardiogram (ECG) sensor, and the second electrode 12e-2 may correspond to a ground electrode of the ECG sensor. The first electrode 12e-1 may make contact with a wrist 50 on one side arm of the user, and the second electrode 12e-2 may make contact with a finger 40 on an opposite side arm of the user.

For example, the smartphone 10f may include a biometric sensor 12f including a first electrode 12f-1 and a second electrode 12f-2. For example, the first electrode 12f-1 may correspond to a reference electrode of an ECG sensor, and the second electrode 12f-2 may correspond to a ground electrode of the ECG sensor. The first electrode 12f-1 may make contact with a finger (not illustrated) on one side of the user, and the second electrode 12f-2 may make contact with a finger (not illustrated) on an opposite side of the user.

Because the biometric sensor 12e and 12f are just connected to or in contact with a surface of the human body, it also may be referred to as a non-invasive sensor. The non-invasive sensor may include a photoplethysmogram (PPG) sensor, an electromyogram (EMG) sensor, a galvanic skin response (GSR) sensor, a non-invasive glucose sensor, an optical body temperature sensor, or a blood pressure sensor, in addition to the ECG sensor. Because the non-invasive sensor may be directly connected to the human body, a medium insertion structure may not be necessary.

As described above, it is essential to supply stable electric power and interrupt external noise so that the biometric sensors 12a, 12b, 12c, 12d, 12e, and 12f measure precise biometric information. If electric power is not stably supplied or external noise is not interrupted, the reliability of the measurement result of the biometric information may be lowered.

For example, the modules 11a, 11c, 11d, and 11e in the smartphone 10a and the smartwatches 10c, 10d, and 10e may consume a relatively large amount of currents temporarily or consistently according to operational states thereof. The modules 11a, 11c, 11d, and 11e may be hardware modules or software modules.

For example, when a camera flash (a hardware module; not illustrated) embedded in the smartphone 10a is operated, a high current may flow instantaneously. Further, when a communication circuit (a hardware module; not illustrated) embedded in the smartphone 10a performs a voice communication, a video communication, or a data communication, a high current may flow through the communication circuit.

Further, for example, the modules 11a, 11c, 11d, and 11e may correspond to high-performance game applications (software modules; not illustrated) that are being performed by processors. Because the high-performance game applications may use high computing resources, a high current may flow through the processor.

In small-sized electronic devices such as the smartphones 10a and the smartwatches 10c, 10d, and 10e, the ground for setting a reference potential may not be sufficiently secured due to a spatial restriction for miniaturization, as compared with general middle or larger-sized electronic devices. Accordingly, when the module 11a, 11c, 11d, and 11e consume a relatively high current, they may generate a change (shaking) in the ground potential. If the ground potential is changed while the biometric sensors 12a, 12c, 12d, and 12e measure biometric information, a voltage or current that is supplied to the biometric sensors 12a, 12c, 12d, and 12e also may be changed. As mentioned above, the change in voltage and current may lower the reliability of the biometric information that is measured by the biometric sensors 12a, 12c, 12d, and 12e.

Further, for example, the biometric sensor 12b of the smartphone 10b is apt to be influenced even by weak noise (for example, conductive noise or radiative noise) due to the high integration, high frequency, and low current design of the circuit. In particular, because the smartphone 10b performs wired and wireless communications, electromagnetic noise may be mixed with a measurement signal while biometric information is measured. Moreover, the electromagnetic noise may directly influence an operation of the biometric sensor (so called, an electromagnetic interference (EMI)). For example, because high-current power may be supplied or data may be transmitted and received at a high frequency through the connection cable 30 of the smartphone 10b, an electromagnetic interference may be generated in the biometric sensor, lowering the reliability of the biometric information.

The noise is not limited to electromagnetic noise. The noise may include noise by vibrations, sounds, or light. For example, if vibrations are generated while the non-invasive biometric sensor measures biometric information, the degree of attachment of the non-invasive biometric sensor to the human body may be changed or the measurement location may be changed, making it difficult to measure precise biometric information. Further, for example, the biometric sensor (for example, a microphone) that measures a breathing sound during sleeping may detect noise due to vibrations or an alarm sound of the electronic device together. Further, for example, the biometric sensor (for example, a PPG sensor or an optical body temperature sensor) using light may detect light generated by an operation of a camera flash or an operation of a display panel as noise together during measurement of biometric information.

Figure 2:
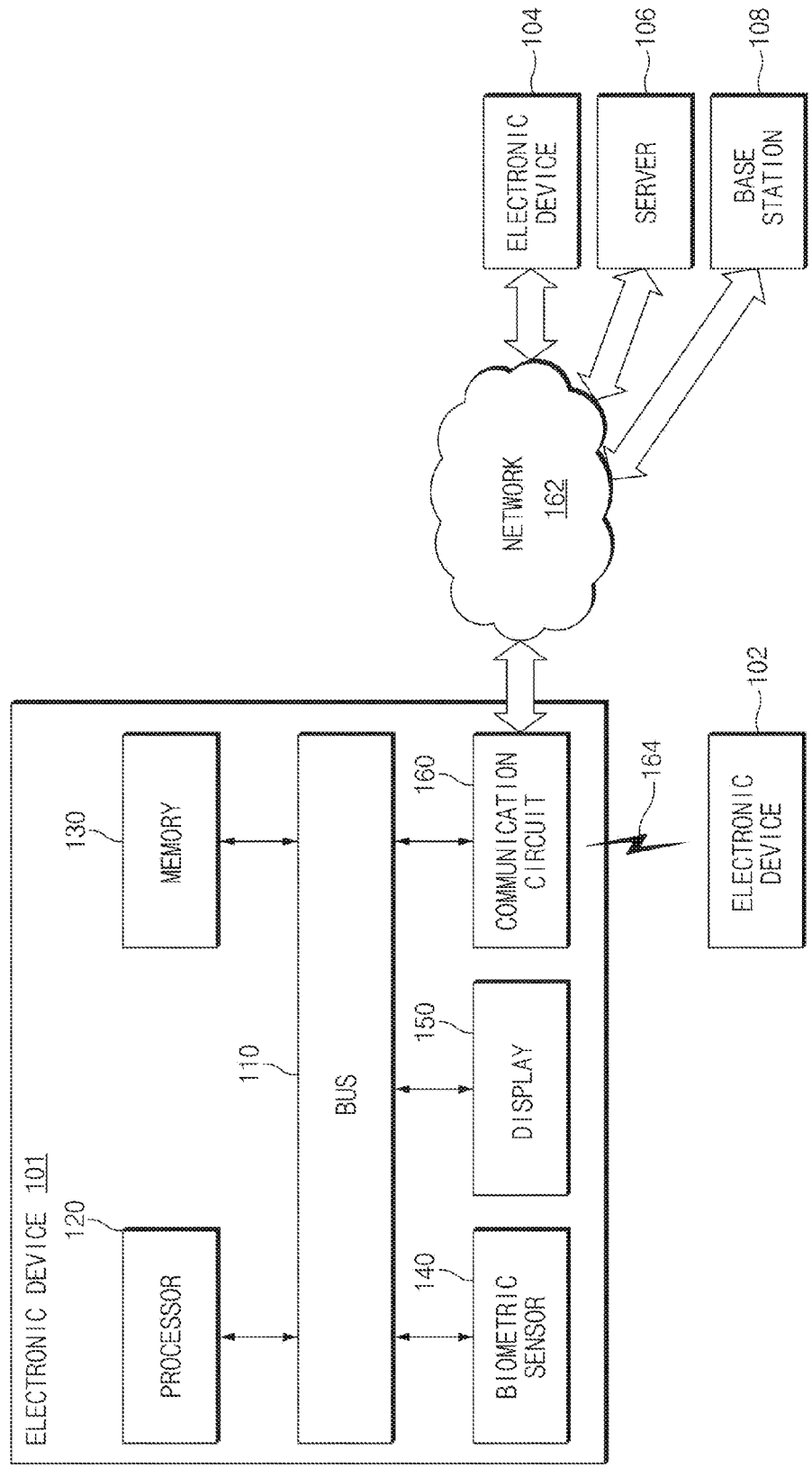
FIG. 2 is a block diagram of an electronic device according to an embodiment of the present disclosure.

FIG. 2 is a block diagram of an electronic device according to an embodiment of the present disclosure.

Referring to FIG. 2, an electronic device 101 may include a bus 110, a processor 120, a memory 130, a biometric sensor 140, a display 150, and a communication circuit 160. In some embodiments of the present disclosure, the electronic device 101 may exclude at least one of the elements or may additionally include another element. For example, the electronic device 101 may further include a notification module that provides a notification related to measurement of biometric information through vibrations or sounds for the user.

The bus 110, for example, may include a circuit that connects the elements 120 to 160 and transfers communications (for example, control messages and/or data) between the elements.

The processor 120 may include one or more of a CPU, an AP, or a communication processor (CP). The processor 120, for example, may execute operations or data processing related to the control and/or communication of a hardware module and a software module of the electronic device 101. The processor 120 may be electrically connected to various elements such as a memory 130 and a sensor module 140, and may execute instructions stored in the memory 130.

For example, the processor 120 may control initiation and termination of a measurement of biometric information of the biometric sensor 140. According to an embodiment of the present disclosure, if the processor 120 acquires an event related to the initiation of a measurement of biometric information, it may deactivate at least some functions of a module or execute an instruction such that the functions remain deactivated.

The module may be a configuration in the electronic device 101 that influences the measurement precision of the biometric sensor 140. For example, the module may include a display 150 and a communication circuit 160, and may include various modules (not illustrated in FIG. 1) provided in the electronic device 101.

In one aspect, as described above, in an operation of the processor 120, the processor 120 may execute an instruction such that some functions of the module are deactivated. However, in another aspect, in an operation of the processor 120, it may be understood that the deactivation operation of the processor 120 activates only the functions of a module (for example, a module used for measurement of biometric information) and deactivates the functions of the other modules.

According to an embodiment of the present disclosure, when the processor 120 deactivates a function of a module, the deactivation operation may be performed in at least two schemes (or modes). For example, the processor 120 receives an event related to initiation of a measurement of biometric information, it may deactivate a function of a module to any one of a first deactivation mode and a second deactivation mode. It may be set by the user which of the first deactivation mode and the second deactivation mode is to be performed.

The first deactivation mode may be a mode in which the processor 120 deactivates all functions of a module. Because the module does not perform any function in the first deactivation mode, a rapid change in current may occur in the module. Accordingly, the biometric sensor 140 may measure biometric information more stably and more precisely in the first deactivation mode than in the second deactivation mode.

According to an embodiment of the present disclosure, if the processor 120 that is operated in the first deactivation mode acquires an event related to initiation of a measurement of biometric information, it may execute an instruction such that a function of a module that uses a higher current than a predetermined current value is to be deactivated. For example, the processor 120 may turn off the module or may not allow any function of the module to be executed.

For example, when the module that uses a higher current than predetermined value is a display 150, the processor 120 may turn off the display 150. Further, when the module that uses a higher current than predetermined value is a graphic processing unit (GPU), the processor 120 may switch off the GPU.

According to an embodiment of the present disclosure, if the processor 120 that is operated in the first deactivation mode acquires an event related to initiation of a measurement of biometric information, it may execute an instruction such that a function of a module that generates noise of an intensity or higher is deactivated.

For example, when the module that generates higher noise than a predetermined value is a communication circuit 160, the processor 120 may not allow any function of the communication circuit 160 to be performed. Accordingly, the processor 120 may extremely lower the intensity of the currents that flow through the communication circuit 160, making the probability of generating noise almost zero.

The module that uses a current of an intensity or higher and the module that uses noise of an intensity or higher are not limited to the above examples. For example, as long as a specific module uses a higher current or generates a higher noise than a predetermined value, the processor 120 may deactivate the functions of the corresponding module. For example, the module may include a motor that provides a vibration notification, an input/output interface (for example, a USB port terminal or a secure digital (SD) card slot) used for a wired connection with an external device, and various biometric sensors (an illuminance sensor, an acceleration sensor, a magnetic sensor, an ultraviolet (UV) sensor, a temperature/humidity sensor, and a gas sensor when glucose information is measured) that are not related to a received event.

The second deactivation mode may be a mode in which the processor 120 deactivates only some functions of the module. For example, some functions of the module that are deactivated by the processor 120 may be limited to a range that does not impair the measurement reliability of biometric information.

According to an embodiment of the present disclosure, the processor 120 that is operated in the second deactivation mode may execute an instruction such that, among the functions of the module, the functions that use a current of an intensity or higher are deactivated.

For example, when the module is the display 150 including a plurality of pixels, the processor 120 may sharply lower a frame rate of a video provided by the display 150 or may an entire part or a part of the screen, which is to be displayed in grayscale. When the display 150 is an active matrix organic light emitting diode (AM-OLED), at least portion of a plurality of pixels thereof may be deactivated (or, switched off), or the intensity (brightness) of light emitted therefrom may be lowered to a predetermined intensity (brightness). When the display 150 is a liquid crystal display (LCD), the intensity (brightness) of light emitted from a backlight unit (BLU) may be lowered to a predetermined intensity (brightness). Accordingly, the intensity of a current used by the display 150 may be lowered to a predetermined value or lower.

Further, for example, when the module is the communication circuit 160, the processor 120 may deactivate at least some of the plurality of functions of the communication circuit 160. For example, the processor 120 may switch off any one of a wired communication function and a wireless communication function of the communication circuit 160, may switch off at least one of a cellular function, a near field communication (NFC) function, a wireless fidelity (Wi-Fi) function, a GNSS function, a Bluetooth function, or an radio frequency (RF) function of the communication circuit 160, or switch off the cellular functions of the communication circuit 160, except for a paging function. Accordingly, the intensity of a current used by the communication circuit 160 may be lowered to a predetermined value or lower, or a probability of generating noise may be lowered.

According to an embodiment of the present disclosure, the processor 120 that is operated in the second deactivation mode may execute an instruction such that, among the functions of the module, the function of generating noise of an intensity or higher is deactivated.

For example, when the module is an audio module (not illustrated), the processor 120 may adjust an audio output function of the audio module to a low level. Further, when the module is a sensor module (not illustrated) that detects a physical quantity at a specific period, the processor 120 may adjust a sensor actuating period of the sensor module to be longer. Accordingly, conductive or radiative noise by power consumption, noise, or actuation of a sensor can be reduced.

According to an embodiment of the present disclosure, the module may correspond to a software module that is executed by the processor 120.

For example, the processor may execute an instruction such that, among a plurality of executed applications, an application that uses more resource (for example, a calculation capacity or a memory space of the processor 120) than a predetermined value is deactivated. The deactivation of some applications may be understood as the deactivation of some functions of the processor 120 that is executing a plurality of applications.

For example, the processor 120 may execute an instruction such that, among the applications that are being executed, the applications that use resources of a size or more, except for the applications (for example, S-Health™) related to measurement of biometric information, are terminated or deactivated. According to a specific embodiment of the present disclosure, the processor 120 may execute an instruction such that all the other applications except for the applications related to measurement of biometric information are terminated.

The other applications, for example, may include a web browsing application, a voice communication application, a notification application, a media player application, a game application, and applications related to exchange of information between the electronic device 101 and external electronic devices 102 and 104, server 106, and base station 108. As a result, the processor 120 may sufficiently secure resources that are used by the applications related to the measurement of biometric information, and also may lower the intensity of a used current and a possibility of generating noise. Through this, the processor 120 can prevent the measurement of biometric information from being stopped or the measurement speed from being delayed due to lack of the resources.

According to a specific embodiment of the present disclosure, the processor 120 of the electronic device 101 may transmit a control message for deactivating modules of other electronic devices 102 and/or 104 that are functionally connected to the electronic device 101 through a network 162 and short range communication 164, to the processors of the other electronic devices 102 and/or 104.

For example, when the electronic device 101 is a smartwatch and the second electronic device 102 is a smartphone, the smartwatch 101 may transmit a control message for deactivating a communication circuit through the short range communication 164 to the smartphone 102. The smartwatch 101 may transmit the control message not to communicate with the smartphone 102 while the biometric information is being measured. Accordingly, the smartwatch 101 may prevent a data communication that causes a high current and high noise in advance during measurement of the biometric information.

Further, according to an embodiment of the present disclosure, the processor 120 may execute an instruction such that, if the measurement of the biometric information is terminated, at least some functions of the module are activated. That is, the processor 120 restore the state of the module to a previous state where an event related to initiation of the measurement of the biometric information has not been received.

Further, according to an embodiment of the present disclosure, the processor 120 may execute an instruction such that, if the measurement of the biometric information is terminated, a module for outputting, storing, or transmitting the measured biometric information is activated. For example, the measurement of the biometric information is terminated, the processor 120 may activate the display 150 and may output the measured biometric information through the display 150. Meanwhile, the processor 120 may activate the module and the module that outputs, stores, or transmits the measured biometric information, at the same time or at different times.

According to a specific embodiment of the present disclosure, if the measurement of the biometric information is terminated, the processor 120 of the electronic device 101 may transmit a control message for activating modules of other electronic devices 102 and/or 104 that are functionally connected to the electronic device 101 through the network 162 and the short range communication 164, to the processors of the other electronic devices 102 and/or 104.

For example, if the electronic device 101 deactivates modules of the other electronic devices 102 and/or 104 by using a specific control message for measurement of biometric information after the termination of measurement of biometric information, it may transmit a control message for activating the deactivated modules again, to the other electronic devices 102 and/or 104.

Further, according to an embodiment of the present disclosure, if the processor 120 acquires an event related to initiation of measurement of biometric information, it may configure a message (for example, a voice message, a video message, a text message, or a data packet), which is supposed to be transmitted to the electronic device 101 (i.e., the destination of the message has been the electronic devices 101), to be transmitted to the second electronic device 102 and/or 104.

That is, if the processor 120 of the electronic device 101 acquires an event related to initiation of the measurement of the biometric information, message forwarding may be set such that a message of which the destination is the electronic device 101 is transmitted to the other electronic devices 102 and/or 104. This is because, if the processor 120 of the electronic device 101 acquires an event related to initiation of a measurement of biometric information, it may deactivate a module and the module may include the communication circuit 160. Accordingly, for example, if a message is transmitted from a base station 108 to the electronic device 101, the other electronic devices 102 and/or 104 may receive the message in place of the electronic device 101.

According to an embodiment of the present disclosure, the processor 120 may transmit control information (so called, forwarding control information) related to reception of a message to the other electronic devices 102 and/or 104, so that a message, which is supposed to be transmitted to the electronic device 101, to be forwarded to the other electronic devices 102 and/or 104. The forwarding control information may be control information for setting the server 106 or the base station 108 such that the server 106 or the base station 108 changes the reception site of a message, which is to be transmitted to the electronic device 101, to the other electronic devices 102 and/or 104.

For example, the forwarding control information may include identification information (for example, subscriber identification information or internet protocol (IP) addresses) of the electronic device 101 and/or the other electronic devices 102 and/or 104, and may include information used to forward a message (or data) to the other electronic devices 102 and/or 104 by the server 106 or the base station 108.

Further, according to an example, the forwarding control information transmitted to the other electronic devices 102 and/or 104 may include an interrupt that activates a communication circuit for receiving the forwarded message. The other electronic devices 102 and/or 104 may activate an embedded communication circuit based on the interrupt, and may receive a message transmitted to the electronic device 101 through the communication circuit.

Further, according to another embodiment of the present disclosure, the processor 120 of the electronic device 101 may directly transmit forwarding control information to the server 106 or the base station 108. In this case, the forwarding control information also may include identification information (for example, subscriber identification information or IP addresses) of the electronic device 101 and/or the other electronic devices 102 and/or 104.

According to an embodiment of the present disclosure, if the measurement of the biometric information is terminated, the processor 120 of the electronic device 101 may configure a message, which is supposed to be transmitted to the other electronic devices 102 and/or 104 (i.e., the destination of the message has been the electronic devices 102 and/or 104), to be transmitted to the electronic device 101 again. That is, the processor 120 of the electronic device 101 may allow a message, which is configured to be forwarded to the other electronic devices 102 and/or 104, to be transmitted to the electronic device 101 again (that is, the message is backwarded to the electronic device 101).

If the measurement of the biometric information is terminated in the electronic device 101, the processor 120 may execute an instruction such that at least some functions of a module (the communication circuit 160) are activated. Accordingly, the processor 120 of the electronic device 101 may establish a communication channel by using the activated communication circuit 160.

The processor 120 may execute an instruction such that the forwarding-back control information is transmitted to the server 106 or the base station 108 through the communication channel. The forwarding-back control information may be control information for setting the server 106 or the base station 108 such that the server 106 or the base station 108 changes the reception site of a message, which is to be transmitted to the electronic device 101, from the other electronic devices 102 and/or 104 to the electronic device 101 again. Similarly, the forwarding-back control information may include identification information of the electronic device 101 and/or the other electronic devices 102 and/or 104. Further, according to an example, the processor 120 of the electronic device 101 may transmit an interrupt for deactivating a communication circuit to the other electronic devices 102 and/or 104. The other electronic devices 102 and/or 104 may deactivate an embedded communication circuit based on the interrupt.

The memory 130 may include volatile and/or nonvolatile memories. For example, the memory 130 may store commands or data for operating and controlling various hardware modules and software modules included in the electronic device 101, including the processor 120, the biometric sensor 140, the display 150, and the communication circuit 160. According to an embodiment of the present disclosure, the memory 130 may store software and/or a program. The program, for example, may include a kernel, middleware, an application programming interface (API), and/or an application program (or "an application"). At least some of the kernel, the middleware, or the API may be referred to as an operating system (OS)(see FIG. 14).

The biometric sensor 140 may be a sensor related to measurement of biometric information. For example, the biometric sensor 140 may include at least one of a glucose sensor, a PPG sensor, an ECG sensor, an EMG sensor, a ballistocardiogram (BCG) sensor, a GSR sensor, an electroencephalogram (EEG) sensor, a blood pressure sensor, a body temperature sensor, an SpO2 sensor, a fingerprint sensor, or an iris sensor.

The biometric sensor 140 may measure biometric information by amplifying a minute change of a parameter that is measured in response to a signal applied to a biometric substance. Alternatively, the biometric sensor 140 may measure biometric information by applying a specific signal to a part of a human body that is a measurement target of biometric information and amplifying a minute change of a parameter that is measured in response to the applied signal.

The measured biometric information may be provided to an element such as the processor 120 or the display 150 in the form of an electrical signal. The biometric information measured by the biometric sensor 140 may include, for example, glucose information, heart pulsation information, electrocardiography information, EMG information, oxygen saturation information, body temperature information, blood pressure information, odor information, fingerprint information, and iris information, such that they correspond to the aforementioned various biometric sensors.

Figure 3:
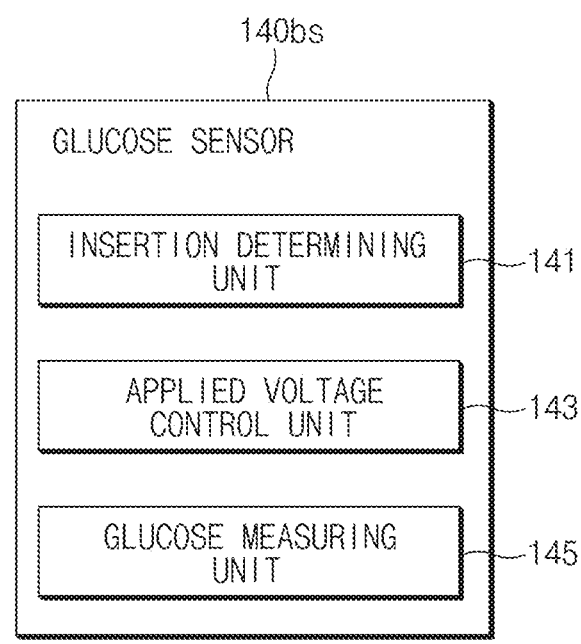
FIG. 3 is a block diagram of a glucose sensor according to an embodiment of the present disclosure.

FIG. 3 is a block diagram of a glucose sensor according to an embodiment of the present disclosure;

Referring to FIG. 3, an invasive glucose sensor 140*bs* is illustrated as an example of the biometric sensor 140. The glucose sensor 140*bs* may include an insertion determining unit 141, an applied voltage control unit 143, and a glucose measuring unit 145.

The insertion determining unit 141 may determine whether a glucose sensor strip (for example, 20 of FIG. 1) is inserted. According to an embodiment of the present disclosure, if the insertion determining unit 141 detects insertion of a glucose sensor strip (for example, insertion of a contact point of an electrode, connection of electric power, or insertion of an optical object), it may notify the user that the glucose sensor strip has been inserted and transmits a measurement initiating event (or an interrupt) for glucose information to the processor 120.

The processor 120, for example, may execute an application related to measurement of glucose based on the event. Subsequently, if the processor 120 detects normal insertion of the glucose sensor strip or blood contained in the glucose sensor strip, it may automatically initiate measurement of glucose information. According to an example, the processor 120 may initiate measurement of glucose information through a user input (for example, selection of an object based on a user interface) after executing an application related to the measurement of glucose. If the measurement of glucose information is initiated, a guidance telling that the measurement of the glucose information is initiated may be displayed on the display 150.

The applied voltage control unit 143 may determine a voltage, which is to be applied, based on an electrode scheme (two electrodes or three electrodes) set for the manufacturer or model. For example, the applied voltage control unit 143 may determine a voltage, which is to be applied to a glucose sensor strip, by identifying configuration information such as information on a working electrode, a counter electrode, and a standard electrode.

The glucose measuring unit 145 may be connected, for example, to a working electrode pin, a counter electrode pin, and a standard electrode pin that electrochemically react with the glucose sensor strip. A glucose oxidation enzyme may be chemically or physically attached to at least one of the electrode pins. The glucose in blood is oxidized by the enzyme in the electrode pin, and an electrical signal is generated as electrons generated by the oxidation reaction are transferred to the electrode pin. The glucose measuring unit 145 may measure the concentration of the glucose in the blood (that is, the value of blood glucose) by processing the electrical signal. The measured blood glucose value may be output through the display 150. Further, the measured blood glucose value may be provided to the processor 120 and may be analyzed through an application regarding the measurement of the biometric information.

Although FIG. 3 illustrates that the biometric sensor 140 corresponds to an invasive glucose sensor 140bs, the biometric sensor 140 may correspond to a non-invasive glucose sensor, into which a glucose sensor strip is not inserted. The non-invasive glucose sensor may not include an insertion determining unit 141, into which the glucose sensor strip is inserted, and various electrode pins electrically connected to the glucose sensor strip. According to various embodiments of the present disclosure, the biometric sensor 140 may correspond to at least one of an E-nose sensor, an EMG sensor, an EEG sensor, an ECG sensor, a BCG sensor, a body temperature sensor, an SpO2 sensor, an iris sensor, a PPG sensor, and a fingerprint sensor.

Moreover, the biometric sensor 140 is not necessarily limited to a sensor related to a live body. For example, the sensor 140 may include at least one of a gesture sensor, a gyro sensor, a pressure sensor, a magnetic sensor, an acceleration sensor, a grip sensor, a proximity sensor, a color sensor (for example, an RGB sensor), a bio sensor, a temperature/humidity sensor, an illumination intensity sensor, and an infrared (IR) sensor or an UV sensor.

The display 150, for example, may include an LCD, a light emitting diode (LED) display, an organic light emitting diode (OLED) display, a microelectromechanical system (MEMS) display, or an electronic paper display. The display 150, for example, may display various contents (for example, a text, an image, a video, an icon, and a symbol) to the user. The display 150 may include a touch screen and receive, for example, a touch, a gesture, a proximity, or a hovering input using an electronic pen or the user's body.

The display 150 may output various pieces of information such as various notification/guide messages, selected objects, and biometric information measurement values, under the control of the processor 120. For example, the display 150 may output various pieces of analysis information such as information telling that the measurement value of biometric information exceeds a standard value.

The communication interface 160, for example, may set and establish a communication between the electronic device 101 and an external device (for example, a first external electronic device 102, a second external electronic device 104, a server 106, or a base station 108). For example, the communication interface 160 may be connected to the network 162 through a wireless communication or a wired communication to communicate with the external device (for example, the second external electronic device 104 or the server 106).

The wireless communication is, for example, a cellular communication protocol, and, for example, may use at least one of long-term evolution (LTE), LTE-advanced (LTE-A), code division multiple access (CDMA), wideband CDMA (WCDMA), a universal mobile telecommunications system (UMTS), wireless broadband (WiBro), or a global system for mobile communications (GSM).

Furthermore, the wireless communication, for example, may include the short range communication 164. The short range communication 164, for example, may include at least one of Wi-Fi, Bluetooth, an NFC, or a GNSS. The GNSS may include at least one of, for example, a global positioning system (GPS), a global navigation satellite system (Glonass), a Beidou navigation satellite system (hereinafter, "Beidou"), or the European global satellite-based navigation system (Galileo), according to an in-use area or a bandwidth. Hereinafter, in the present disclosure, the "GPS" may be interchangeably used with the "GNSS".

The wired communication may include at least one of, for example, a USB, a high definition multimedia interface (HDMI), recommended standard-232 (RS-232), and a plain old telephone Service (POTS). The network 162 may include at least one of communication networks, for example, a computer network (for example, a local area network (LAN) or a wide area network (WAN)), the Internet, or a telephone network.

The first and second external electronic devices 102 and/or 104 may be the same or different type devices from the electronic device 101. According to an embodiment of the present disclosure, the server 106 may include a group of one or more servers. According to various embodiments of the present disclosure, all or some of the operations executed by the electronic device 101 may be executed by another or a plurality of electronic devices (for example, the electronic devices 102 and 104 or the servers 106). According to an embodiment of the present disclosure, when the electronic device 101 should execute some functions or services automatically or upon request, it may request at least some functions associated with the functions or services from another device (for example, the electronic devices 102 and 104 or the server 106), in place of or in addition to directly executing the functions or services. The second electronic device (for example, the electronic device 102 or 104 or the server 106) may execute a requested function or an additional function, and may transfer the result to the electronic device 101. The electronic device 101 may process the received result directly or additionally, and may provide a requested function or service. To this end, for example, the cloud computing, distributed computing, or client-server computing technologies may be used.

Figure 4:
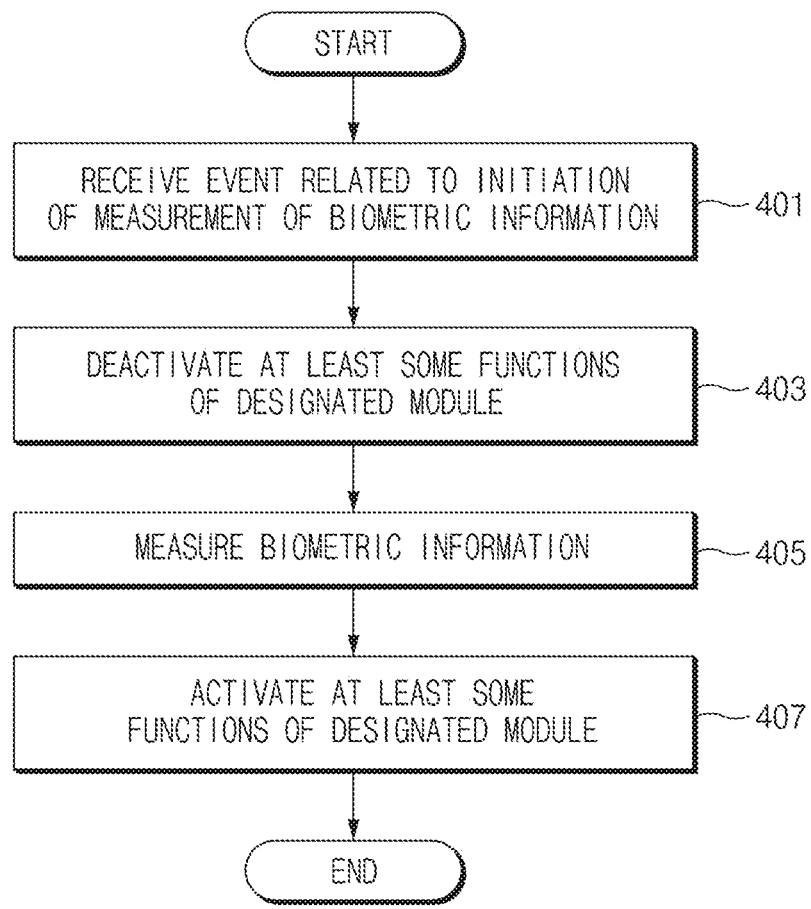
FIG. 4 is a flowchart of a method for measuring biometric information according to an embodiment of the present disclosure.

FIG. 4 is a flowchart of a method for measuring biometric information according to an embodiment of the present disclosure.

Referring to FIG. 4, the method for measuring biometric information according to an embodiment of the present disclosure may include operations 401 to 407.

In operation 401, the electronic device 101 may receive an event (an interrupt) related to initiation of a measurement of biometric information. The event related to initiation of a measurement of biometric information may be acquired or received in various schemes.

For example, the electronic device 101 may acquire the event related to initiation of a measurement of biometric information if a biometric substance that is a measurement target of biometric information is received (for example, insertion of a glucose sensor strip is detected), a user input (for example, a user interface such as a voice recognition, a button, or a touch) is received, or a measurement target (for example, a human body) of biometric information is connected to the electronic device (101) (for example, detection of an AC component due to a contact of ECG leads (electrodes) with the human body or a contact of a finger with a PPG sensor).

Further, for example, the electronic device 101 may acquire an event related to initiation of a measurement of biometric information based on a measurement value of another pieces of biometric information. If a blood pressure value that is monitored by a blood pressure sensor is lowered to a value or less, the electronic device 101 may initiate measurements of glucose and ECG.

Further, the electronic device 101 may acquire an event related to initiation of a measurement of biometric information based on a measurement value related to a movement of the user. For example, if a rapid movement of the user (for example, a rapid change in speed or a rapid change in acceleration) is detected by an acceleration sensor or a gyro sensor, the electronic device 101 may initiate measurements of heart pulsations or an ECG.

Further, the event related to initiation of a measurement of biometric information may be acquired through an interaction with other electronic devices 102 and/or 104. For example, the event related to initiation of a measurement of biometric information may be received through the short range wireless communication 164 (for example, Bluetooth or NFC), or the network 162. Further, the event related to initiation of a measurement of biometric information may be acquired when a private authentication (for example, PIN authentication, fingerprint authentication, or iris authentication) of the user is performed.

Further, the event related to initiation of a measurement of biometric information may be acquired through an interaction with other applications. According to an embodiment of the present disclosure, the user (a measurement target of biometric information) may designate a time (for example, a specific time, thirty minutes before dinner, or thirty minutes after dinner) or a site (for example, a hospital or a fitness center) when or where biometric information will be measured in advance, by using a schedule management application. The event related to initiation of a measurement of biometric information may be acquired from the schedule managing application when it comes to the time or site. That is, the event may be received based on a preset time or the site where the user carrying the electronic device 101 is located. According to some embodiments of the present disclosure, the event related to initiation of a measurement of biometric information may be periodically acquired at a time interval.

If a user input regarding initiation of a measurement is received through an application (for example, S-Health™) related to a measurement of biometric information or an user input regarding initiation of biometric information is received through a voice input (for example, S-Voice™), the electronic device 101 may acquire an event related to initiation of a measurement of biometric information. The application related to the measurement of biometric information may be executed by selecting an object (for example, an application icon or a widget) that is displayed on a part of a screen (for example, a home screen or a locking screen) output on the display 150.

In operation 403, the electronic device 101 may deactivate at least some functions of the module. For example, the module may correspond to a module that uses a higher current than a predetermined current value or generates a higher noise than a predetermined value. Further, the module may correspond to a module that uses a resource of a predetermined size or more. According to an example, the deactivation function may correspond to a function that uses a current or resource of an intensity or higher or generates noise, among various functions of the module.

According to an embodiment of the present disclosure, in operation 403, the electronic device 101 may perform an initiation operation (for example, calibration of the biometric sensor 140) for measuring biometric information.

Further, according to an embodiment of the present disclosure, when the module is the communication circuit 160, in operation 403, the electronic device 101 may perform an operation of setting forwarding of a message (or data) before the communication circuit 160 is deactivated. Meanwhile, the operation of deactivating the communication circuit 160 may correspond to an operation of setting an airplane mode.

According to various embodiments of the present disclosure, in operation 403, the electronic device 101 may not deactivate the module and not measure biometric information in despite of the event received in operation 401 (in the result, the the electronic device 101 maintain a standby state or an activation state). For example, when an event related to initiation of a measurement of biometric information (for example, heart pulsation information) is set to be periodically acquired, the electronic device 101 may not measure the biometric information if the module (for example, a communication circuit) is operated even though the measurement period is reached. This case, for example, may correspond to a case when the priority of an operation of the module is higher than that of the measurement of biometric information.

In operation 405, the electronic device 101 may measure biometric information. According to an example, the biometric information may include at least one of glucose information, heart pulsation information, electrocardiography information, EMG information, brain wave information, BCG, GSR, oxygen saturation information, body temperature information, blood pressure information, odor information, fingerprint information, or iris information.

In operation 407, if the measurement of the biometric information is completed, the electronic device 101 may activate at least some functions of the module deactivated in operation 403. Accordingly, the electronic device 101 may restore to a state before the measurement of the biometric information. To achieve this, according to a specific embodiment of the present disclosure, the identifiers (IDs) of the hardware modules and/or the software modules that have been deactivated before the measurement of the biometric information and state information (for example, setting information or operation information of a wireless communication circuit) before the deactivation maybe stored in the memory 130 of the electronic device 101 or a storage of the server 106 in advance.

Figure 5:
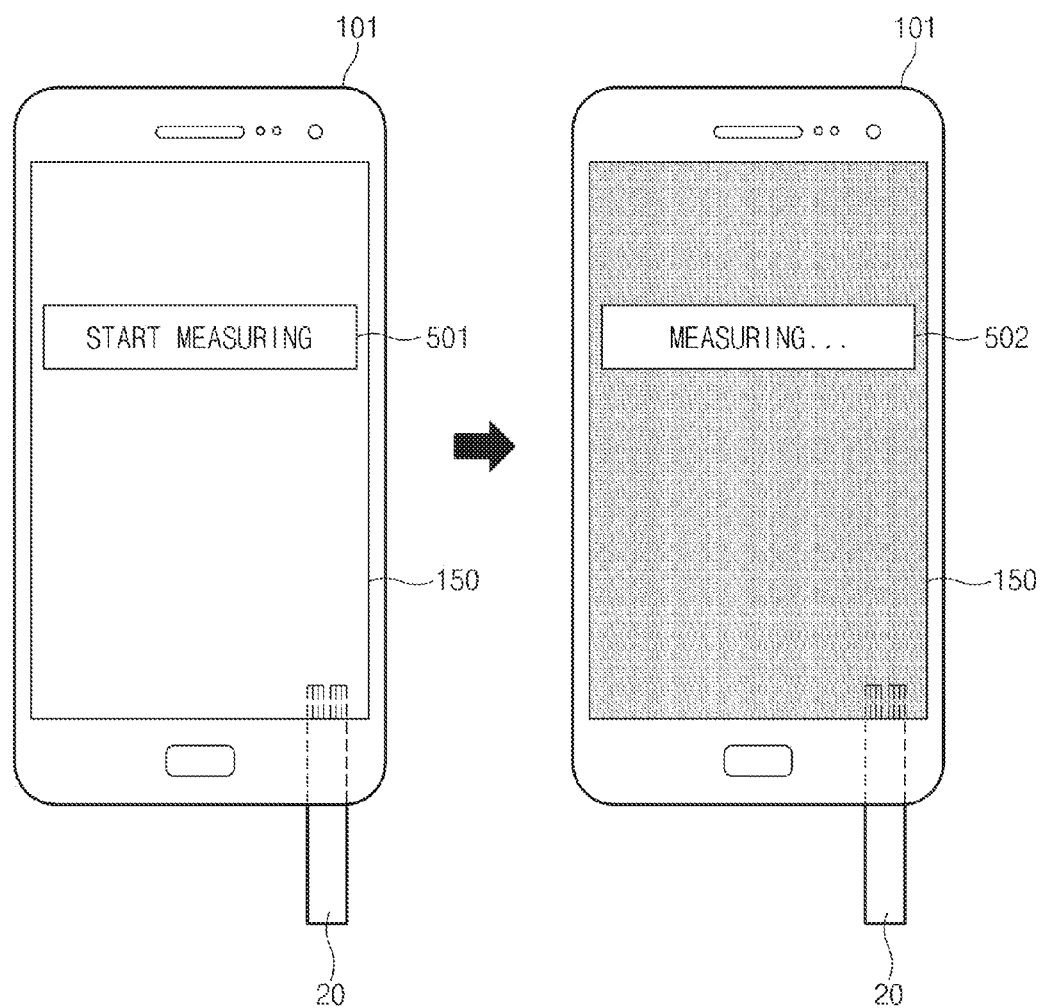
FIG. 5 is a view illustrating a case in which a module is a display according to an embodiment of the present disclosure.

FIG. 5 is a view illustrating a case in which a module is a display according to an embodiment of the present disclosure.

Referring to FIG. 5, an electronic device 101 is illustrated in which an application related to measurement of biometric information is being executed. The electronic device 101 may receive a user input for an object 501 that represents a start of a measurement, as an event related to initiation of a measurement of biometric information (see operation 401 of FIG. 4). For example, the measurement may be in regard to a glucose sensor strip 20 inserted in the electronic device 101.

If the user input for the object 501 is received, at least a part (that is, a part of the screen 150 except for the object 502) of the display 150 that is the module may be deactivated such that an image is not output (see operation 403 of FIG. 4). According to an embodiment of the present disclosure, the at least a part of the display 150 may be changed from a color that consumes much power to a color (for example, black or gray) that consumes little power. Additionally or alternatively, the brightness of the at least a part of the display 150 may be set to a low level to lower power consumption.

Thereafter, if the biometric information is measured (see operation 405 of FIG. 4) and the measurement of the biometric information is completed, the part of the screen 150 except for the object 502 may be activated again (see operation 407 of FIG. 4).

Figure 6:
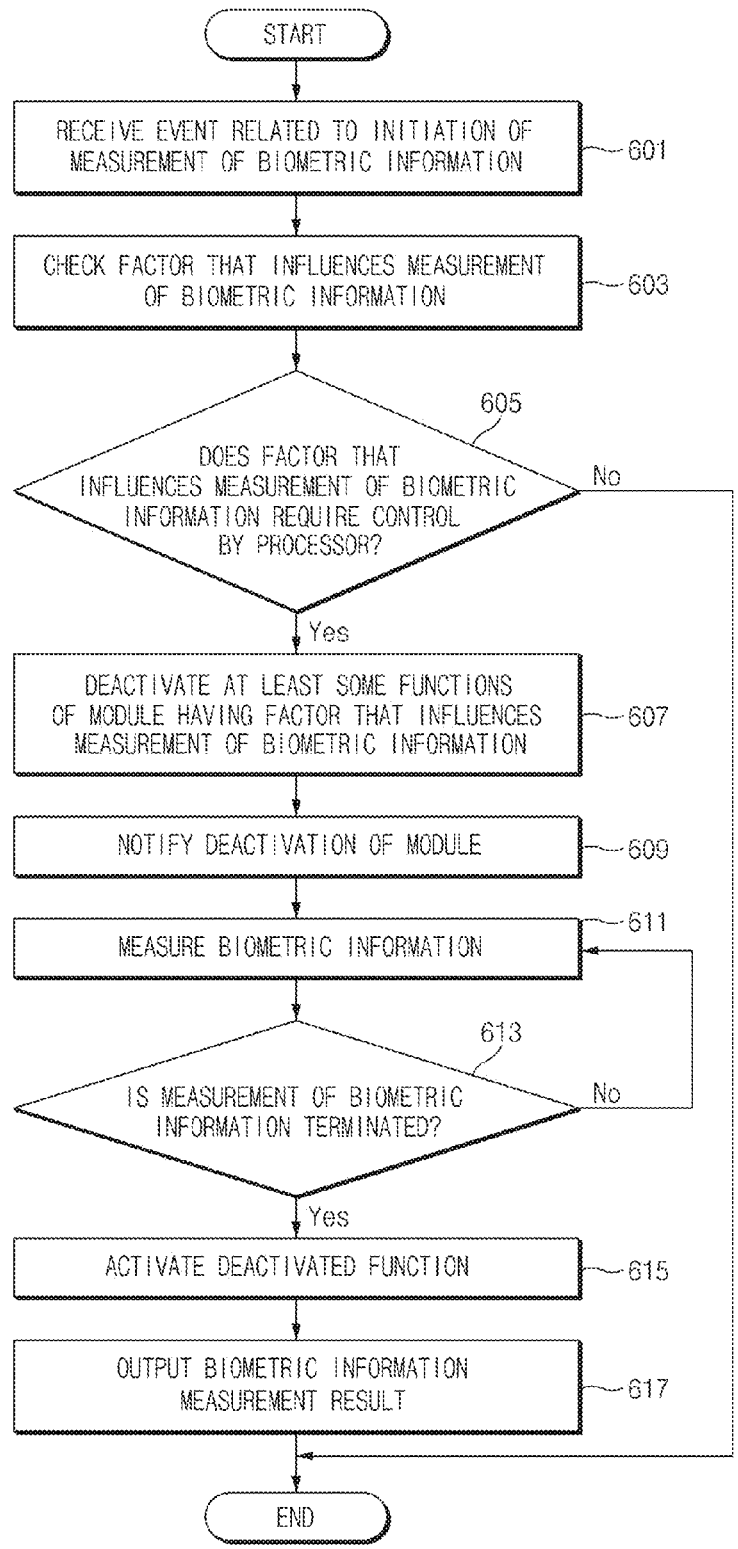
FIG. 6 is a flowchart of a method for measuring biometric information according to another embodiment of the present disclosure.

FIG. 6 is a flowchart of a method for measuring biometric information according to another embodiment of the present disclosure.

Referring to FIG. 6, the method for measuring biometric information according to the other embodiment of the present disclosure may include operations 601 to 617. A repeated description related to the operations of FIG. 4 may be omitted.

In operation 601, the electronic device 101 may receive an event related to initiation of a measurement of biometric information.

In operation 603, a factor that influences the measurement of biometric information may be checked. For example, the electronic device 101 may check a state of a module that may influence the measurement of biometric information.

For example, the module that influences the measurement of biometric information may include a module that consumes relatively high power or an instantaneously high current or voltage, a module that uses many resources of the electronic device 101, and/or a module that generates noise that influences the measurement of biometric signals.

For example, the display 150 that reproduces a video, the communication circuit 160 that performs a voice/video communication or a data communication, an audio module that generates audio signals at a high output, a camera flash module that generates light at an instantaneous high current or voltage, various sensor modules that periodically convert physical quantities into electrical signals, a battery charging module that receives power of a high current and a high voltage, a motor that generates physical vibrations by using a high current, a wired input/output interface that transmits and receives a large amount of data to and from the outside (for example, a USB port module, a serial port module, a parallel port module, a HDMI terminal module, a USIM slot module, or a SD card slot module), and a game application that uses a considerable number of resources may correspond to the module that influences the measurement of biometric information.

Further, in operation 603, the electronic device 101 may check an environmental factor that influences the measurement of biometric information with an embedded sensor.

For example, the environmental factor that influences the measurement of the biometric information may be detected by a rear cover coupling detecting sensor that optically or electrically detects a spaced distance between a rear cover and the body of the electronic device 101, a temperature sensor that determines overheating of the interior of the electronic device 101, a humidity sensor that determines a humid state of the interior of the electronic device 101, an acceleration sensor or gyro sensor that detects a rapid motion of the electronic device 101, a gyro sensor, and a module for detecting a charging level of a battery.

In operation 605, the electronic device 101 may determine whether the factor that influences the measurement of biometric information needs to be controlled by the processor 120. That is, prior to the measurement of biometric information, it may be determined whether the environment for a precise measurement is determined under the control of the processor 120. The factor that influences the measurement of biometric information may be determined based on a condition for guaranteeing the reliability of the measurement of biometric information, a condition for performing a biometric information measuring process, a condition for operating a biometric sensor, a condition for a medical device approval standard, or the like.

When the factor that influences the preciseness of the measurement of biometric information needs to be controlled by the processor 120, the process may proceed to operation 607. However, when the factor that influences the measurement of biometric information does not need to be controlled by the processor 120, the electronic device 101 may terminate the method for measuring biometric information according to the present embodiment of the present disclosure, after providing a guide message for the user.

For example, if the rear cover of the electronic device 101 is opened, the internal temperature of the electronic device 101 is detected to be a value (for example, 42 degrees Celsius) or more, the internal humidity of the electronic device 101 is detected to be a value or more, another piece of biometric information is being measured, the electronic device 101 is rapidly moved at a predetermined value or more, or the charging level of the battery is a value (for example, 1% or less), the control by the processor 120 may be unnecessary or impossible. Accordingly, the electronic device 101 may output a factor that influences the measurement of biometric information and a guide of solving the factor on the display 150 as a guide message, and then terminate the method for measuring biometric information according to the present embodiment of the present disclosure.

For example, if the rear cover of the electronic device 101 is opened, and then the spaced distance between the body and the rear cover of the electronic device exceeds a medical device approval standard, a control by the processor 120 may be impossible. In this case, the electronic device 101 outputs a guide message telling that the spaced distance between the body and the rear cover exceeds the medical device approval standard on the display 150, and may terminate the measurement of biometric information.

The various factors that make a control by the processor 120 unnecessary may be examples. For example, when a cooling module is provided in the interior of the electronic device 101 even though the internal temperature of the electronic device 101 is detected to be a value or more, an operation of measuring biometric information through the control of the cooling module may be performed. For example, when a drying module is provided in the interior of the electronic device 101 even though the internal humidity of the electronic device 101 is detected to be a value or more, an operation of measuring biometric information through the control of the drying module may be performed.

In operation 607, the electronic device 101 may deactivate at least some function of the module that has a factor that influences the measurement of biometric information. The module that has a factor that influences the measurement of biometric information may include the communication circuit 160.

For example, if the communication circuit 160 is not performing a voice communication or a data communication, the electronic device 101 may deactivate the functions of the communication circuit 160. If the communication circuit 160 performs a voice communication or a data communication, the electronic device 101 may deactivate the communication circuit 160 after the voice communication or the data communication is terminated. Alternatively, even though the communication circuit 160 is performing a voice communication or a data communication, the electronic device 101 may immediately terminate the voice communication or the data communication and deactivate the communication circuit 160

According to an embodiment of the present disclosure, in operation 607, the electronic device 101 may display a guide message by which continuation of an operation, termination after completion of an operation, or immediate termination of an operation of the communication circuit 160 on the display.

In operation 609, the electronic device 101 may notify the user of the deactivation of the module that has a factor that influences the measurement of biometric information, through various notification units. For example, the electronic device 101 may notify the user of the deactivation through at least one of the display 150 that provides a visual notification, an audio module that provides an audible notification, or a motor that generates vibrations that provide a haptic notification.

According to an embodiment of the present disclosure, a notification operation of operation 609 may be omitted based on a usage situation of the electronic device. For example, when the measurement of biometric information starts and the electronic device 101 enters into an airplane mode (for example, deactivation of the communication circuit 160), the electronic device 101 actually enters into the airplane mode but may display to the user as if the mode is not an airplane mode. That is, the user may not detect whether the module is deactivated during the measurement of biometric information.

In operation 611, the electronic device 101 may measure biometric information. According to an embodiment of the present disclosure, the electronic device 101 may notify the user of various states (initiation of a measurement, continuation of a measurement, termination of a measurement, or the like) of the measurement of biometric information of the biometric sensor 140 through various notification units.

In operation 613, the electronic device 101 may determine whether the measurement of biometric information that has been described in operation 611 is terminated. If the measurement of biometric information is not terminated (No in operation 613), the measurement of biometric information of operation 611 may be continued. Meanwhile, if the measurement of the biometric information is terminated (Yes in operation 613), the process may proceed to operation 615.

In operation 615, if the measurement of the biometric information is completed, the electronic device 101 may activate one or more functions of the module deactivated in operation 607. If a module for outputting, storing, or transmitting the biometric information measured in operation 611 is included in the deactivated modules, the electronic device 101 also may activate the module for outputting, storing, or transmitting the measured biometric information.

According to an embodiment of the present disclosure, if one or more functions of the module deactivated in operation 607 are activated, the operation that has been stopped for the measurement of the biometric information may be subsequently performed. For example, if the communication circuit 160 has stopped a data communication for measurement of biometric information, it may resume the stopped data communication.

In operation 617, the electronic device 101 may output a measurement result and/or an analysis result of the biometric information. For example, the measurement and/or the analysis result of the biometric information may be output by at least one of the modules activated in operation 615. According to an embodiment of the present disclosure, the measurement result and/or the analysis result of the biometric information may be stored in the memory 130 or may be transmitted to the other electronic devices 102 and/or 104.

Figure 7:
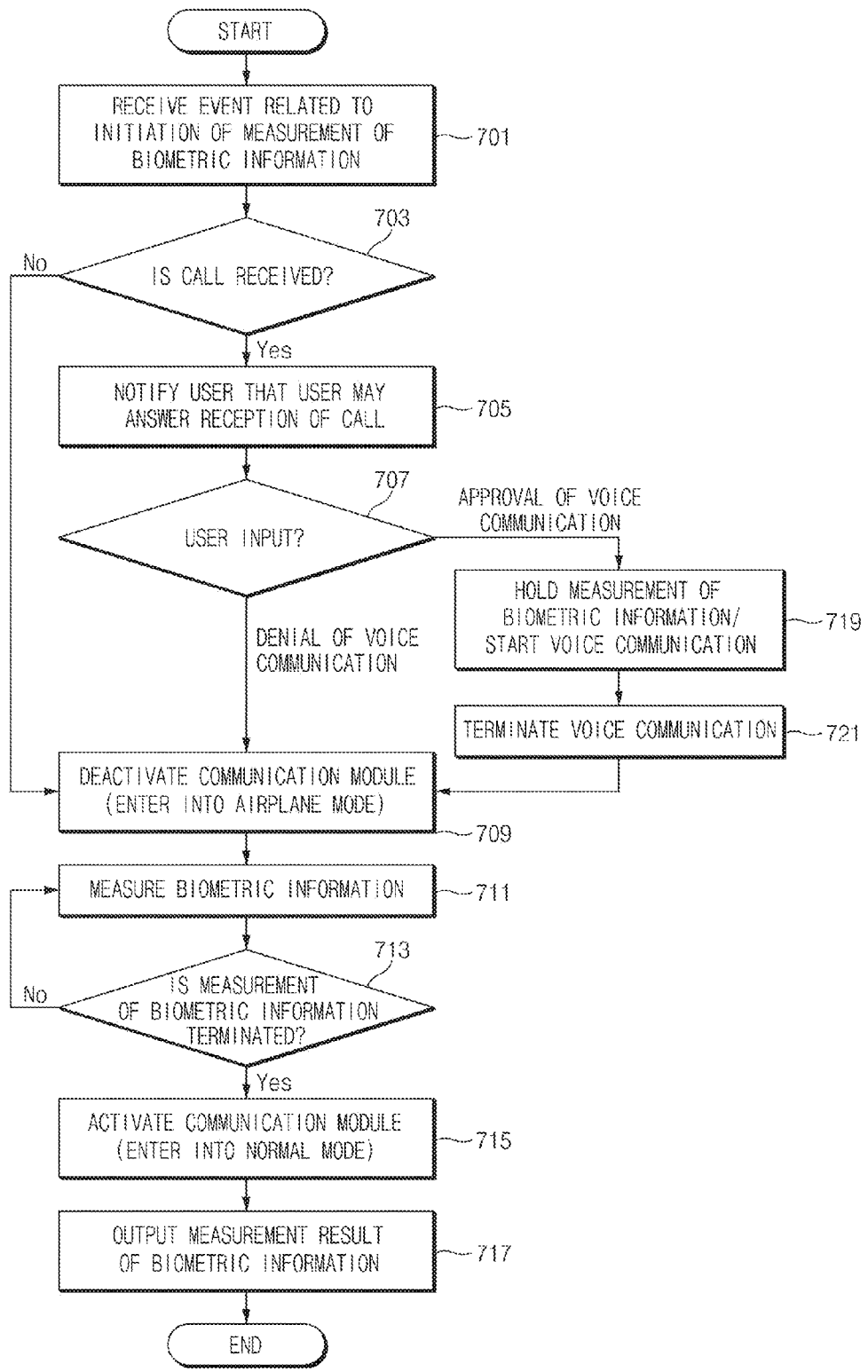
FIG. 7 is a flowchart illustrating a relationship between a method for measuring biometric information and a communication service according to an embodiment of the present disclosure.

FIG. 7 is a flowchart illustrating a relationship between a method for measuring biometric information and a communication service according to an embodiment of the present disclosure.

Referring to FIG. 7, the flowchart illustrating the relationship between the method for measuring biometric information according to an embodiment of the present disclosure and the communication service may include operations 701 to 721. Although FIG. 7 illustrates that the communication service is a voice communication service based on a cellular mobile communication, the present disclosure is not limited thereto. The communication service may include a short messaging service (SMS and multimedia messaging service (MMS)), a voice communication/video communication service through a 3rd generation (3G) mobile communication network, a voice communication/video communication service (VoLTE and Voice over LTE) through an LTE mobile communication network, a voice communication service by an over-the-top (OTT) service provider, a video communication service, an instant messaging service, and a social network service (SNS). Meanwhile, a repeated description related to the operations of FIGS. 4 and 6 may be omitted.

In operation 701, the electronic device 101 may receive an event related to initiation of a measurement of biometric information. For example, the event may be generated by providing the electronic device 101 with a medium (for example, a glucose sensor strip) including a biometric substance, or by connecting a measurement target (for example, the human body) of biometric information to the electronic device 101 (for example, a lead of an ECG sensor).

In operation 703, the electronic device 101 may determine whether a call is received. If the electronic device 101 has received a call (i.e., an incoming call), the process may proceed to operation 705. Meanwhile, if the electronic device 101 has not received a call, the process may proceed to operation 709 and operations 709 to 717 may be performed.

In operation 705, the electronic device 101 may notify the user that the user may answer the reception of the call, through the display 150. For example, as illustrated in FIG. 8, the electronic device 101 may output a guide message 801 asking the user of whether the user will answer the reception of the call, on a display 150.

Figure 8:
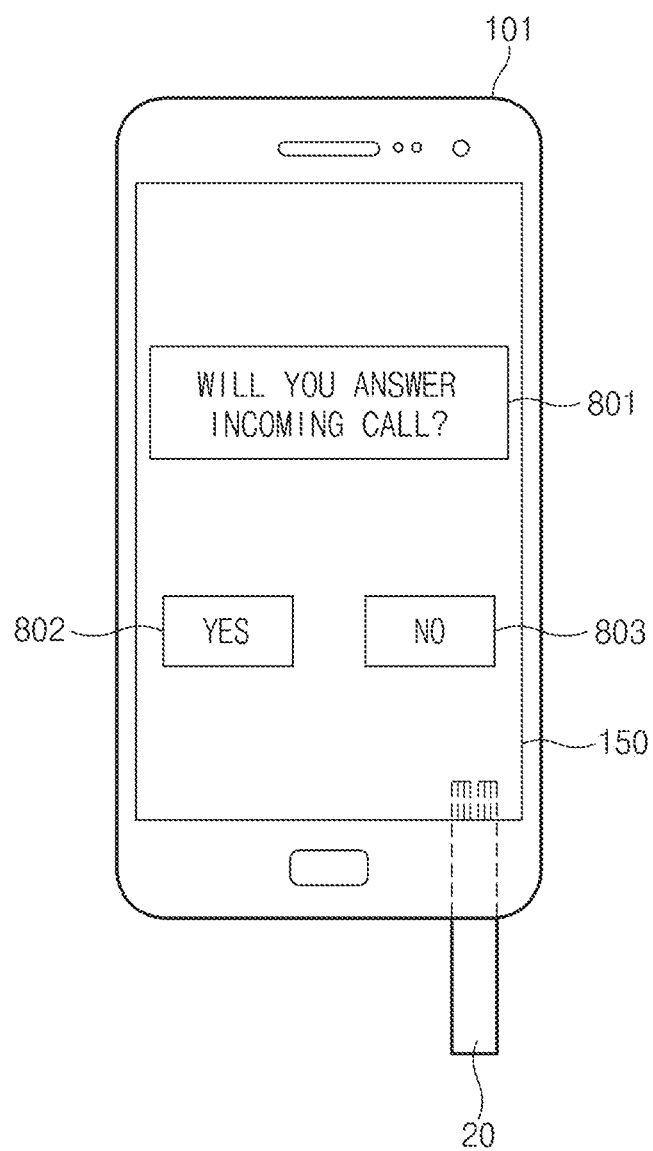
FIG. 8 is a view illustrating a display of an electronic device according to an embodiment of the present disclosure.

FIG. 8 is a view illustrating a display of an electronic device according to an embodiment of the present disclosure.

Referring to FIG. 8, an electronic device 101 is illustrated in which an application related to measurement of biometric information is being executed. The measurement may be in regard to a glucose sensor strip 20 inserted in the electronic device 101.

In operation 707, the electronic device 101 may receive an input regarding whether the user will answer the reception of the call, from the user. For example, referring to FIG. 8, the user may select an object 802 that represents approval of a voice communication or an object 803 that represents denial of a voice communication.

If the object 802 that represents approval of a communication is selected, the process may proceed to operation 719, and if the object 803 that represents denial of a communication, the process may proceed to operation 709.

In operation 709, the electronic device 101 may deactivate at least some functions of the communication circuit 160. The communication circuit 160 may correspond to a module that responds to the call received in operation 703 to perform a voice communication. According to an embodiment of the present disclosure, an operation of deactivating at least some functions of the communication circuit 160 may correspond to entering into an airplane mode.

In operation 711, the electronic device 101 may measure biometric information.

In operation 713, the electronic device 101 may determine whether the measurement of biometric information has been terminated. If the measurement of biometric information is not terminated (No in operation 713), the measurement of biometric information of operation 711 may be continued. Meanwhile, if the measurement of biometric information has been terminated, the process may proceed to operation 715.

In operation 715, if the measurement of the biometric information is completed, the electronic device 101 may activate at least some functions of the communication circuit 160 deactivated in operation 709. According to an embodiment of the present disclosure, operation 715 may correspond to an operation of releasing the airplane mode and entering into a normal mode.

In operation 717, the electronic device 101 may output a measurement result and/or an analysis result of the biometric information. According to an embodiment of the present disclosure, the measurement result and/or the analysis result of the biometric information may be output on the display 150, may be stored in the memory 130, or may be transmitted to the other electronic devices 102 and/or 104. According to some embodiments of the present disclosure, operation 717 may be performed prior to operation 715.

According to an embodiment of the present disclosure, the electronic device may acquire an event related to termination of a measurement of biometric information, before or after operation 717. For example, the event related to termination of a measurement of biometric information may be generated by eliminating a medium containing a biometric substance from the electronic device 101, detaching the electronic device 101 from a measurement object of biometric information, or completing calculation of the measurement result of biometric information.

According to an embodiment of the present disclosure, if an event related to termination of a measurement of biometric information is acquired, the electronic device 101 may ask the user of whether the user will additionally measure biometric information, through various notification units. If the electronic device 101 receives a user input related to an additional measurement of biometric information, it may perform operations 709 to 717. When a user input related to a failure of an additional measurement of biometric information is received or a user input is not received for a specific time period, the method for measuring biometric information according to the present embodiment may be terminated.

In operation 719, the electronic device 101 may hold the measurement of biometric information and may start a voice communication in response to the reception of the call.

If the voice communication is terminated in operation 721, the electronic device 101 may proceed to operation 709 and may perform operations 709 to 717.

FIG. 7 illustrates that a call is received after the event related to the measurement of biometric information is received. However, according to an embodiment of the present disclosure, a call may be received in advance and a voice communication is performed before the event related to the measurement of biometric information is received. In other words, an event related to the measurement of biometric information may be received during a voice communication. In this case, the electronic device 101 may notify the user that the measurement of biometric information cannot be made based on the event and may continue to perform the voice communication. Alternatively, the electronic device 101 may hold a measurement of biometric information based on the event, and may initiate measurement of biometric information with the deactivation of the communication circuit 160 after the voice communication is terminated.

The electronic device according to some embodiments may measure biometric information sufficiently precisely even though a voice communication and a measurement of biometric information are performed together. According to the electronic device, even though the user answers for the voice communication in operation 707, an operation of measuring biometric information in operation 711 and the following operations may be performed.

Figure 9:
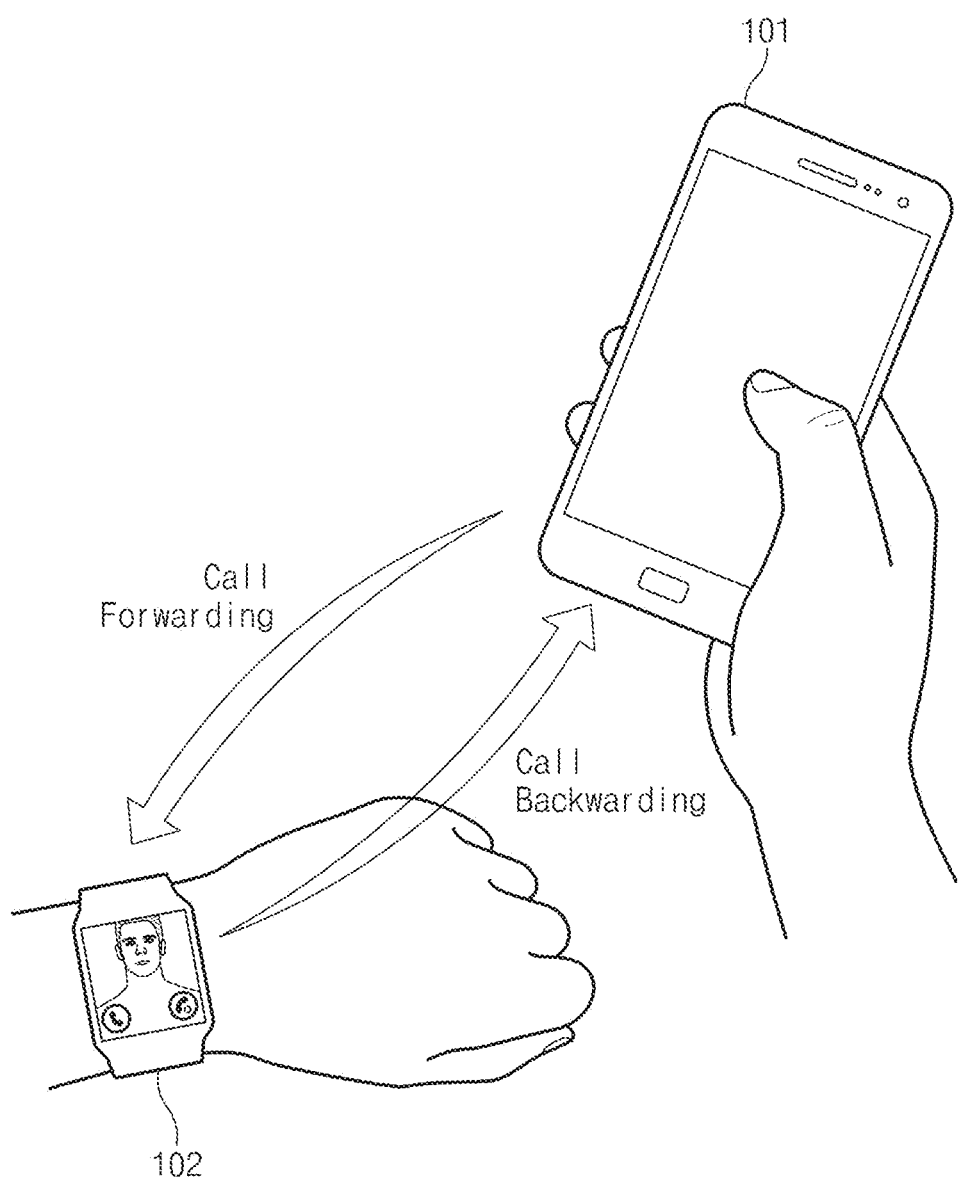
FIG. 9 is a view illustrating a call/message forwarding operation according to an embodiment of the present disclosure.

FIG. 9 is a view illustrating a call/message forwarding operation according to an embodiment of the present disclosure.

Referring to FIG. 9, the call/message forwarding (and/or backwarding) operation according to an embodiment of the present disclosure may be performed at least between a first electronic device 101 and a second electronic device 102 (a detailed forwarding/backwarding operation will be described in regard to FIGS. 10 and 11).

The first electronic device 101 or the second electronic device 102 may deactivate the embedded communication circuit 160 for consideration the measurement preciseness of biometric information. Accordingly, the first electronic device 101 cannot receive a communication message (for example, voice/video communication data based on a 3G or VoLTE network, voice/video communication data based on mVoIP, data packets, an instant message (IM) message, an SMS/MMS message, or an SNS message) that is transmitted to the first electronic device 101 while the biometric information is measured. However, because it is difficult for another user to recognize whether the first electronic device 101 is measuring biometric information, the other user cannot take, for example, an urgent contact with the user of the electronic device 101.

Accordingly, if the first electronic device 101 according to an embodiment of the present disclosure receives an event regarding initiation of a measurement of biometric information, it may configure a communication message, which is supposed to be transmitted to the first electronic device 101, to be transmitted to the second electronic device 102 (so called, message forwarding). Further, if the first electronic device 101 has measured biometric information and then has terminated the measurement of biometric information, the first electronic device 101 may configure a communication message, which is supposed to be transmitted to the second electronic device 102, to be transmitted to the first electronic device 101 (so called, message backwarding). The first electronic device 101 may perform message forwarding before the measurement of biometric information, and may perform message backwarding after the measurement of biometric information. Accordingly, the first electronic device 101 may solve a problem (for example, a failure of reception of a call or a message) caused by the communication circuit 160.

For example, the message forwarding operation may be an operation that configures a communication message, of which the reception site (or destination) is set to the first electronic device 101 to be transmitted to the second electronic device 102, in the base station 108 or the server 106 that establishes a communication channel. For example, if a cellular message is forwarded (so called, call forwarding) from the first electronic device 101 to the second electronic device 102, a call for the first electronic device 101 may be transmitted to the second electronic device 102 and the second electronic device may perform an incoming call based on the call.

Further, the message backwarding operation may be an operation that performing the message forwarding operation in a reverse way. That is, the message backwarding operation may be an operation that configures a communication message, of which the reception site (or destination) is the first electronic device 101, not the second electronic device 102 but to the first electronic device 101 in the base station 108 or the server 106. For example, if the message backwarding operation is performed after the message forwarding (so called, call forwarding) from the first electronic device 101 to the second electronic device 102, a call for the first electronic device 101 may be received by the first electronic device 101.

Figure 10:
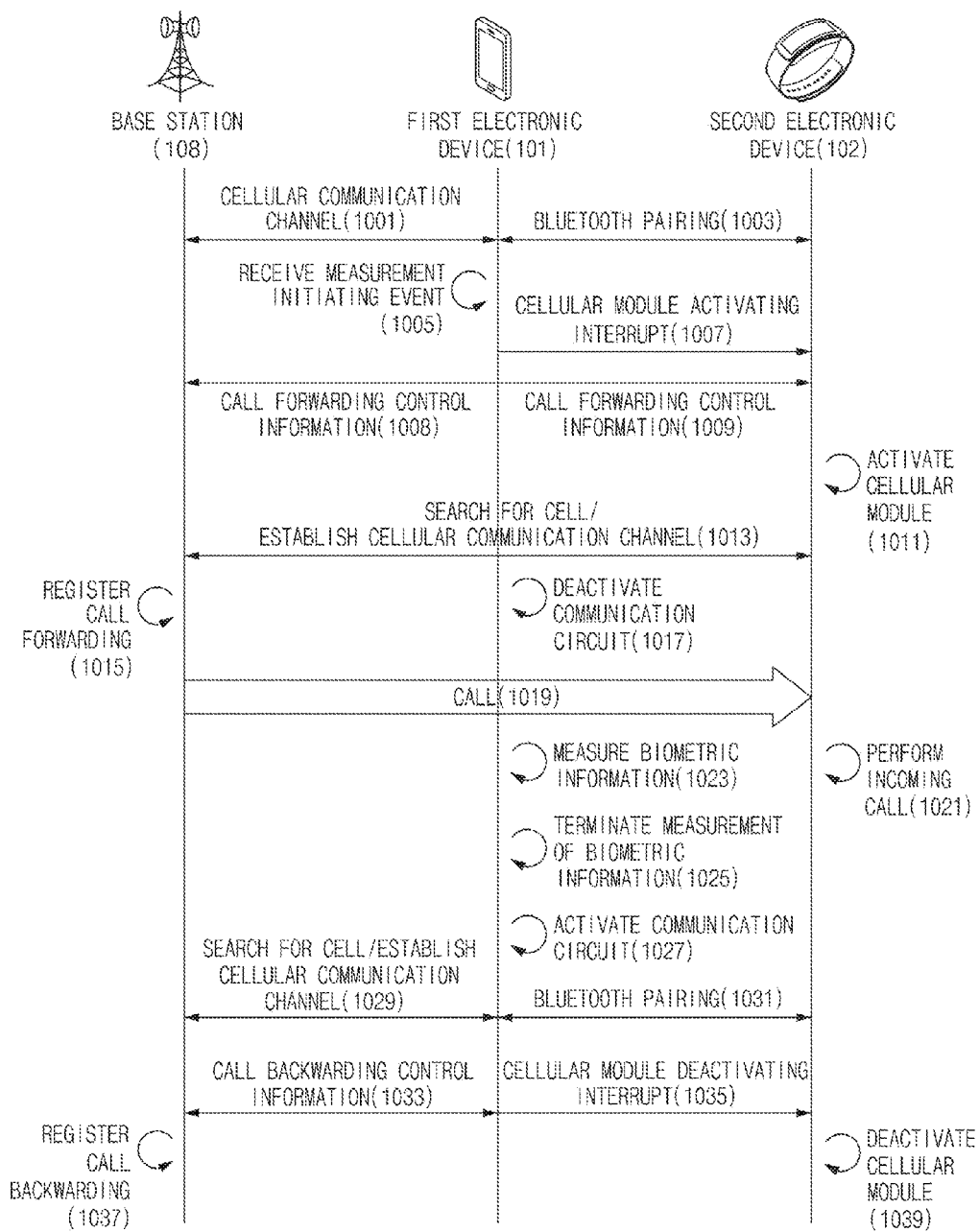
FIG. 10 is a view illustrating respective operations of message forwarding according to an embodiment of the present disclosure.

FIG. 10 is a view illustrating respective operations of message forwarding according to an embodiment of the present disclosure.

Referring to FIG. 10, the message forwarding (and/or backwarding) according to an embodiment of the present disclosure may be performed between the first electronic device 101, the second electronic device 102, and the base station 108. For example, the first electronic device 101 may be a smartphone, and the second electronic device 102 may be a smartwatch on which a cellular module is mounted. Further, the base station 108 may represent a base station apparatus that manages a cellular communication (for example, 3G/4G) in a specific area (cell). A detailed description in relation to FIGS. 4, 6, and 7 may be omitted.

In operation 1001, a cellular communication channel may be established between the first electronic device 101 and the base station 108. The first electronic device 101 may form a cellular channel (a pilot channel, a synchronization channel, a paging channel, or a traffic channel) with the base station 108. By forming the cellular channel, the electronic device 101 may maintain a state in which an incoming call and an outgoing call may be performed.

In operation 1003, the electronic device 101 and the second electronic device 102 may be connected to each other through a short range communication unit. For example, the first electronic device 101 and the second electronic device 101 may be paired through the Bluetooth to transmit and receive data and/or information.

In operation 1005, the first electronic device 101 may receive an event related to initiation of a measurement of biometric information. If the event is received, the electronic device 101 may configure a call (or message), which is supposed to be transmitted to the electronic device 101, to be transmitted to the second electronic device 102 (a call forwarding operation). According to an embodiment of the present disclosure, the call forwarding operation may include an operation of transmitting control information related to the reception of a call (or message) of the first electronic device 101 to the base station 108 and/or the second electronic device 102. For example, the call forwarding operation may include operations 1007 to 1009.

In operation 1007, the first electronic device 101 may transmit an interrupt for activating the communication circuit to the second electronic device 102. The interrupt may correspond to an interrupt that activates the communication circuit of the second electronic device 102 used for reception of the call (message). For example, the interrupt may correspond to an interrupt that activates the cellular module included in the communication circuit of the second electronic device 102.

In operation 1008, the first electronic device 101 may transmit call forwarding control information to the base station 108. For example, the call forwarding control information may include information (for example, subscriber identification information, an IP address, or a MAC address) of the second electronic device 102 and/or various commands related to the setting of the call forwarding.

In operation 1009, the first electronic device 101 may transmit control information (call forwarding control information) related to reception of a call (message) even to the second electronic device 102. For example, the call forwarding control information transmitted to the second electronic device 102 may include subscriber identification information of the first electronic device 101, base cell information (for example, cell IDs), and/or various control commands used for the second electronic device 102 in related to call forwarding.

Although FIG. 10 illustrates that operation 1008 and operation 1009 are performed at the same time, they may be performed at different times or selectively. Further, although it has been described that operation 1009 is performed after operation 1007, the operation sequence of operation 1009 and operation 1007 is not limited thereto. Operation 1009 may be performed before operation 1007. An interrupt of operation 1007 may be included in call forwarding control information of operation 1009.

In operation 1011, the second electronic device 102 may activate the communication circuit (for example, the cellular module) in response to the interrupt of operation 1007.

In operation 1013, the second electronic device 102 may search for a cell that is covered by the base station 108, and may establish a cellular communication channel (or a link) with the base station 108 based on the call forwarding control information received in operation 1009.

In operation 1015, the base station 108 may register call forwarding from the first electronic device 101 to the second electronic device 102. That is, the base station 108 may change the reception site of a communication message, which is to be transmitted to the first electronic device 101, to the second electronic device 102. Accordingly, if another user's electronic device transmits a call to the first electronic device 101, the corresponding call may be transmitted to the second electronic device 102.

According to a specific embodiment of the present disclosure, the base station 108 may provide an automatic response function that notifies that the first electronic device 101 cannot receive a call without performing the call forwarding.

In operation 1017, the first electronic device 101 may deactivate the communication circuit 160. According to an embodiment of the present disclosure, the first electronic device 101 may deactivate all functions of the communication circuit 160 including a cellular communication function and a Bluetooth pairing function. According to another embodiment of the present disclosure, the electronic device 101 may release all channels other than a paging channel of the cellular communication function.

In operation 1019, the base station 108 may transmit a call (message) transmitted from another device to the first electronic device, to the second electronic device 102.

In operation 1021, the second electronic device 102 may perform an incoming call based on the call transmitted in operation 1019. The incoming call may be performed through the cellular communication channel established in operation 1013.

In operation 1023, the first electronic device 101 may measure biometric information.

In operation 1025, the first electronic device 101 may terminate the measurement of biometric information. If the measurement of the biometric information is terminated, the first electronic device 101 may perform an operation (a call backwarding operation) of configuring a call (communication message), which is supposed to be transmitted to the second electronic device 102, to be transmitted to the first electronic device 101. According to an embodiment of the present disclosure, the call backwarding operation may include an operation of transmitting control information related to the reception of a call (communication message) of the first electronic device 101 to the base station 108. For example, the call backwarding operation may include operations 1029 to 1033.

In operation 1027, the first electronic device 101 may activate the communication circuit 160 deactivated in operation 1017.

In operation 1029, the first electronic device 101 may search for a cell of the base station 108. This is because the communication circuit 160 is activated in operation 1027. Further, the first electronic device 101 may establish a cellular communication channel with the base station 108 that has been released in operation 1017, again.

In operation 1031, the first electronic device 101 may establish Bluetooth pairing with the second electronic device 102 that has been released in operation 1017, again.

In operation 1033, the first electronic device 101 may transmit call backwarding control information to the base station 108. The call backwarding control information may include information corresponding to the call forwarding control information. According to an embodiment of the present disclosure, the first electronic device 101 may transmit call backwarding control information to the second electronic device 102. In this case, the second electronic device 102 may transmit the call backwarding control information to the base station 108.

In operation 1035, the first electronic device 101 may transmit an interrupt related to deactivation of the cellular module to the second electronic device 102. Because the user of the second electronic device 102 may be the same as the user of the first electronic device 101, the cellular module for the second electronic device may be switched off. In some embodiments of the present disclosure, operation 1035 may be omitted.

In operation 1037, the base station 108 may register call backwarding. That is, the base station 108 may change the reception site of a communication message, which is to be transmitted to the first electronic device 101, from the second electronic device 102 to the first electronic device 101. Accordingly, if another user transmits a call to the first electronic device 101, the corresponding call may be transmitted to the first electronic device 101.

In operation 1039, the second electronic device 102 may deactivate the embedded cellular module in response to the reception of the interrupt in operation 1035. Meanwhile, if the second electronic device 102 is performing a voice communication, it may defer the deactivation of the embedded cellular module.

Figure 11:
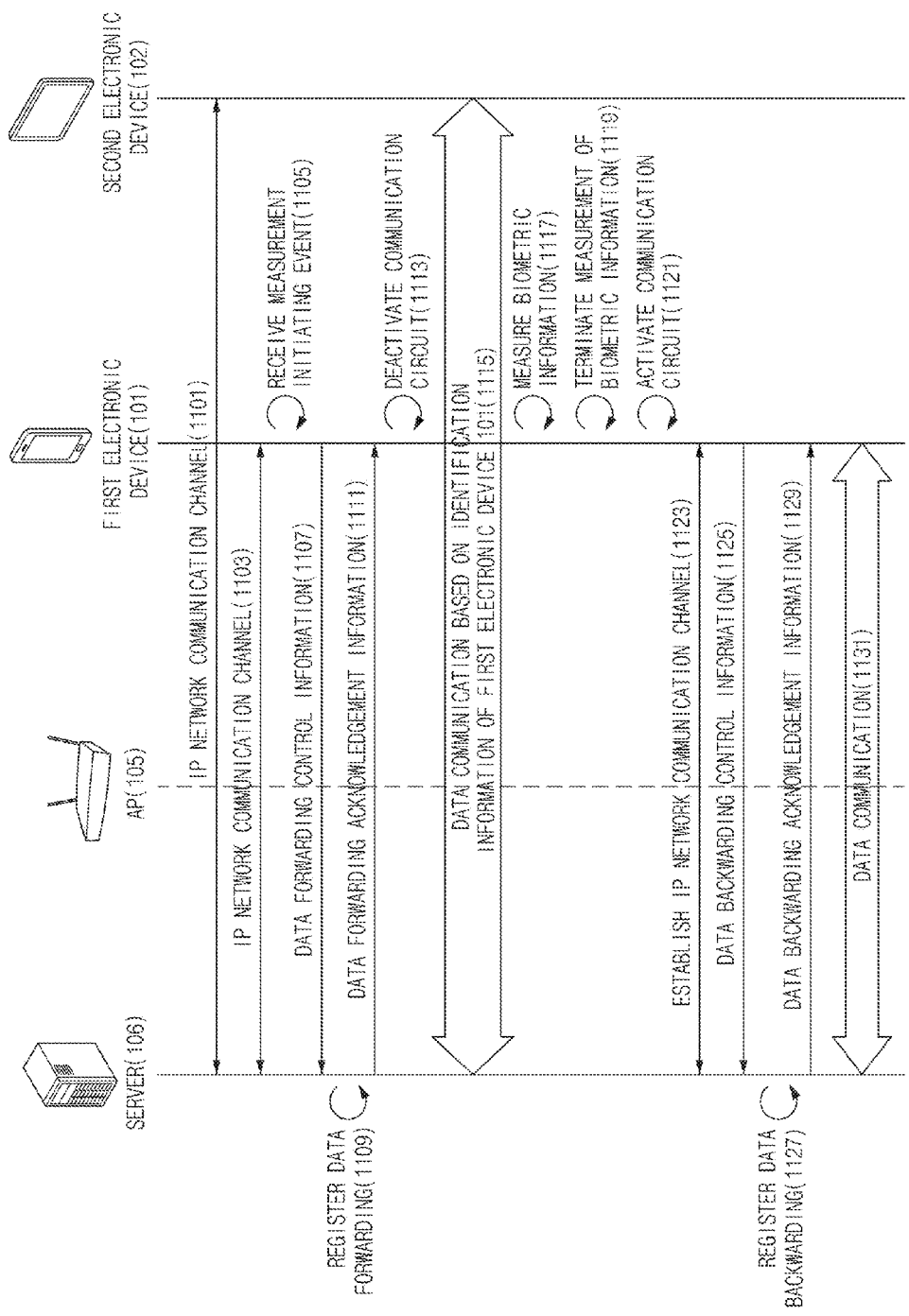
FIG. 11 is a view illustrating respective operations of data forwarding according to an embodiment of the present disclosure.

FIG. 11 is a view illustrating respective operations of data forwarding according to an embodiment of the present disclosure.

Referring to FIG. 11, the data forwarding (and/or backwarding) according to an embodiment of the present disclosure may be performed between the first electronic device 101, the second electronic device 102, an access point (AP) 105, and the server 106. For example, the first electronic device 101 may be a smartphone, and the second electronic device 102 may be a tablet PC on which a Wi-Fi module is mounted. Further, the server 106 may be, for example, one of an instant messaging management server, an SNS server, a VoIP management server, and an mVoIP management server. The AP may be included in an IP network between the first electronic device 101, the second electronic device 102, and the server 106. Meanwhile, a repeated description in relation to FIGS. 4, 6, and 7 may be omitted.

In operation 1101, an IP network communication channel may be established between the second electronic device 102 and the server 106.

In operation 1103, an IP network communication channel may be established between the first electronic device 101 and the server 106. That is, the first electronic device 101, the second electronic device 102, and the server 106 may be mutually connected to each other, for example, through a network based on an IP.

In operation 1105, the first electronic device 101 may receive an event related to initiation of a measurement of biometric information. If the event is received, the electronic device 101 may allow a data packet (or communication message), which is to be transmitted to the electronic device 101, to be transmitted to the second electronic device 102 (a data forwarding operation). The data forwarding operation may include operations 1107 to 1111.

In operation 1107, the first electronic device 101 may transmit data forwarding control information to the server 106. The data forwarding control information may correspond to control information for allowing the second electronic device 102 to receive a data packet (communication message), of which the reception site is the first electronic device 101. For example, the data forwarding control information may include identification information (for example, subscriber identification (SID) information, an IP address, or a MAC address) of the first electronic device 101 and/or the second electronic device 102, identification information (for example, an IP address or a uniform resource identifier (URI) of the server 106, and/or various control commands used by the server 106 in relation to data forwarding.

In operation 1109, the server 106 may register data forwarding from the first electronic device 101 to the second electronic device 102. That is, the server 106 may change the reception site of a data packet, which is to be transmitted to the first electronic device 101, to the second electronic device 102. Accordingly, if another user transmits an instant message to the first electronic device 101, the corresponding instant message may be transmitted to the second electronic device 102.

According to a specific embodiment of the present disclosure, the server 106 may not perform the data forwarding. The server 106 may separately maintain a data packet transmitted to the first electronic device 101, and may transmit the maintained data packet to the first electronic device 101 when the communication channel with the first electronic device 101 is established again.

In operation 1111, the server 106 may transmit data forwarding acknowledgement information to the first electronic device 101. The data forwarding acknowledgement information may function to report that the data forwarding operation is completed.

In operation 1113, the first electronic device 101 may deactivate the communication circuit 160. For example, the first electronic device 101 may deactivate the communication circuit 160 (for example, a Wi-Fi module) in response to the reception of the data forwarding identification information.

In operation 1115, the second electronic device 102 may perform a data communication (that is, transmission/reception of a data packet) based on the identification information of the first electronic device 101. The data packet may include, for example, a voice/video communication data packet based on an mVoIP service, various multimedia message data packets based on an SMS or an IM, or an Internet data packet. The data communication may be performed through an IP network communication channel that has been established in operation 1101.

In operation 1117, the first electronic device 101 may measure biometric information.

In operation 1119, the first electronic device 101 may terminate the measurement of biometric information. If the measurement of the biometric information is terminated, the first electronic device 101 may perform an operation (a data backwarding operation) of configuring a data packet (message), which is to be transmitted to the second electronic device 102, to be transmitted to the first electronic device 101. The data backwarding operation may include operations 1121 to 1129.

In operation 1121, the first electronic device 101 may activate the communication circuit 160 (for example, a Wi-Fi module) deactivated in operation 1113.

In operation 1123, the first electronic device 101 may establish (or recover) an IP network communication channel with the server 106 that has been released due to operation 1113. This is because the communication circuit 160 is activated in operation 1121.

In operation 1125, the first electronic device 101 may transmit data backwarding control information to the server 106. The data backwarding control information may include information corresponding to the data forwarding control information.

In operation 1127, the server 106 may register data backwarding. That is, the server 106 may change the reception site of a data packet, which is to be transmitted to the first electronic device 101, from the second electronic device 102 to the first electronic device 101. Accordingly, if another user transmits an instant message to the first electronic device 101, the corresponding instant message may be transmitted to the first electronic device 101.

In operation 1129, the server 106 may transmit data backwarding acknowledgement information to the first electronic device 101. The data backwarding acknowledgement information may function to report that the data backwarding operation is completed.

In operation 1131, the first electronic device 101 may perform a data communication with the server 106 based on the identification information of the first electronic device 101. That is, the first electronic device 101 may perform a data communication with the server 106, as before the measurement of biometric information.

Figure 12:
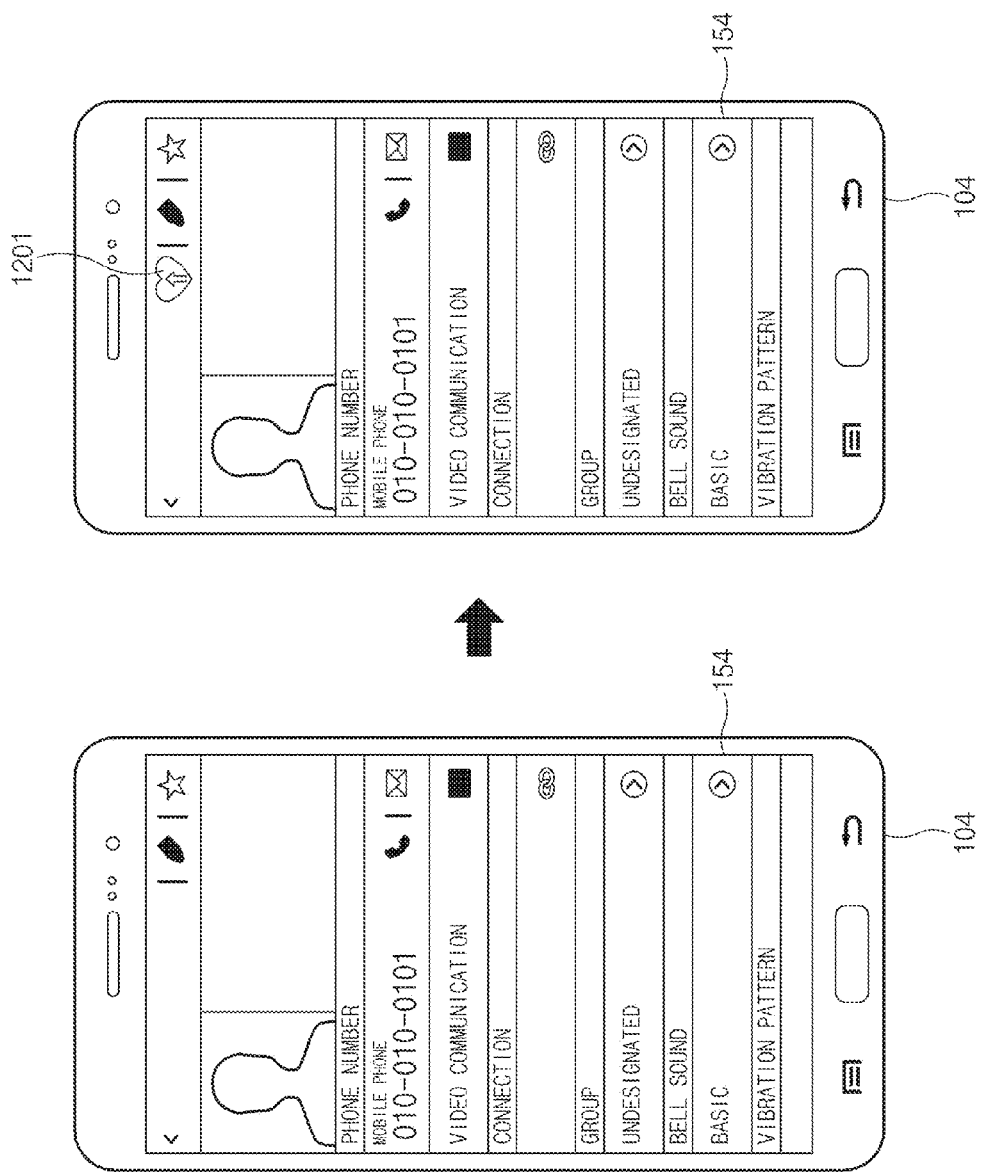
FIG. 12 is a view illustrating an electronic device of another user when a message forwarding operation is performed according to an embodiment of the present disclosure.

FIG. 12 is a view illustrating an electronic device of another user when a message forwarding operation is performed according to various embodiments of the present disclosure.

Referring to FIG. 12, a third electronic device 104 of another user is illustrated when the message forwarding according to various embodiments of the present disclosure is performed. For example, the user of the third electronic device 104 may identify a contact address of the user of the first electronic device 101 by executing a contact application. A contract address and a profile of the user of the first electronic device 101 are output on the display 154 of the third electronic device 104. The state of the user of the first electronic device 101 displayed on the display 154 may be updated in real time.

Further, according to an embodiment of the present disclosure, the message forwarding control information of FIGS. 10 and 11 may contain information that represents the state of the electronic device. For example, the message forwarding control information may include a state message telling that the electronic device is currently measuring biometric information.

In performing operation 1015 or operation 1109, the base station 108 of FIG. 10 or the server 106 may register state data telling that the user of the first electronic device 101 is currently measuring biometric information in a contact address database, based on the acquired message forwarding control information. If the base station 108 or the server 106 registers the state data, the information based on the state data may be updated in a contacts application of the third electronic device 104.

According to an embodiment of the present disclosure, the third electronic device 104 may display an available communication means (for example, one or more of a call forwarding message, an SNS message, an SMS message, and an ARS message) of the first electronic device 101 as state information of the user of the first electronic device 101, through an icon 1201.

The third electronic device 104 on the left side may represent a state before the state data are registered in the contact address database, and the third electronic device 104 on the right side may represent a state after the state data are registered in the contact address database. The user of the third electronic device 104 may recognize state information of the user of the first electronic device 101, that is, that the user of the first electronic device 101 is currently measuring biometric information, through the icon 1201 of FIG. 12. Further, a call is given to the user of the third electronic device 104, the user may recognize that call forwarding will be performed or an ARS message will be provided.

Figure 13:
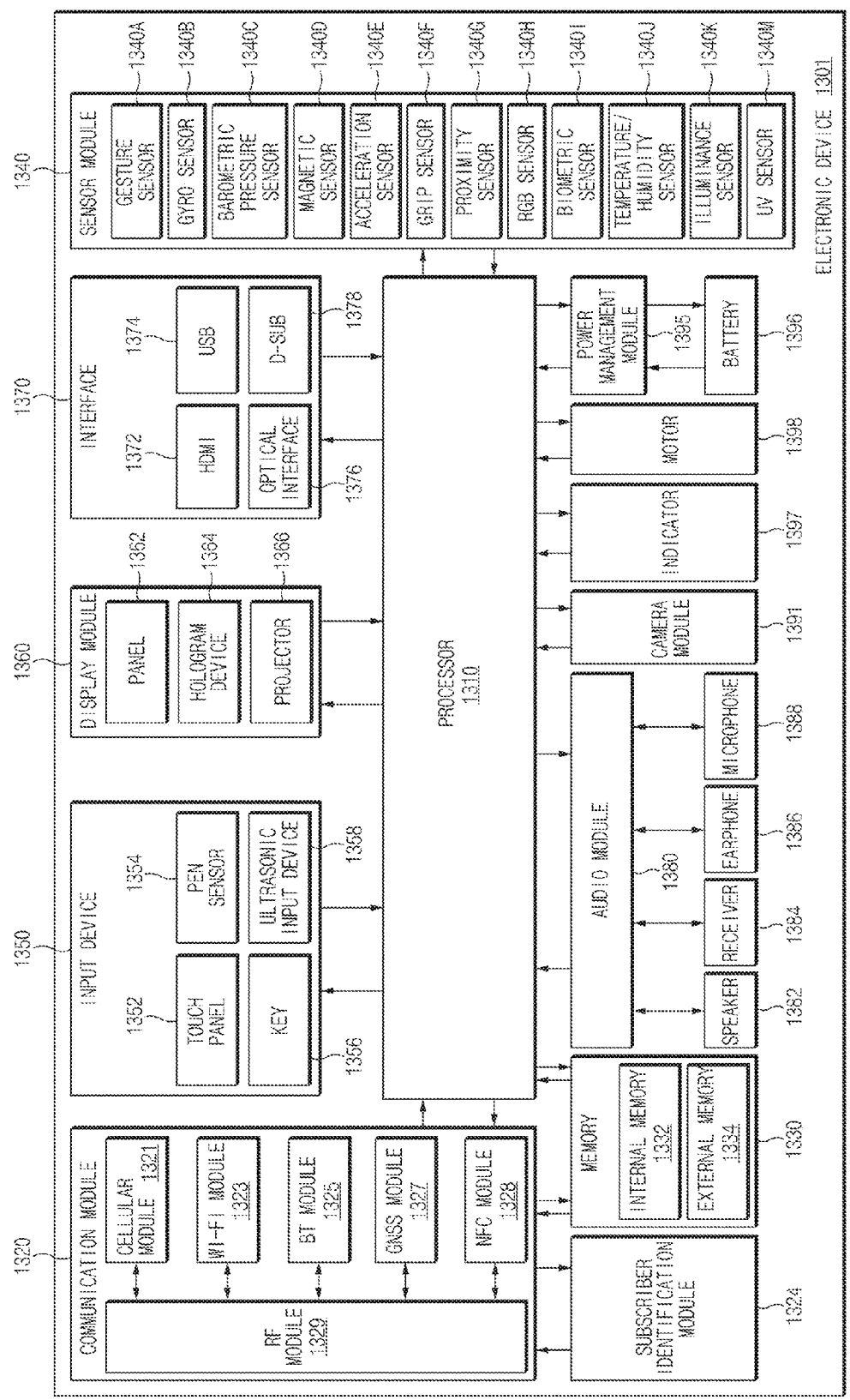
FIG. 13 is a block diagram of an electronic device according to various embodiments of the present disclosure.

FIG. 13 is a block diagram of an electronic device 1301 according to various embodiments of the present disclosure.

Referring to FIG. 13, an electronic device 1301 may include, for example, all or some of the electronic devices 101, 102, and 104 illustrated in FIG. 2. Referring to FIG. 13, the electronic device 31 may include at least one processor (for example, an AP 1310), a communication module 1320, a subscriber identification module (SIM) card 1324, a memory 1330, a sensor module 1340, an input device 1350, a display module 1360, an interface 1370, an audio module 1380, a camera module 1391, a power management module 1395, a battery 1396, an indicator 1397, or a motor 1398.

The processor 1310 may control a plurality of hardware or software components connected to the processor 1310 by operating an OS or an application program and perform a variety of data processing and calculations. The processor 1310 may be implemented by, for example, a System on Chip (SoC). According to an embodiment of the present disclosure, the processor 1310 may further include a graphical processing unit (GPU) and/or an image signal processor. The processor 1310 may include at least some of the elements illustrated in FIG. 2. The processor 1310 may load instructions or data, received from at least one other component (for example, a non-volatile memory), in a volatile memory to process the loaded instructions or data, and may store various types of data in a non-volatile memory.

The communication module 1320 may have the same or similar structure to the communication interface 160 of FIG. 2. The communication module 1320 may include, for example, a cellular module 1321, a Wi-Fi module 1323, a Bluetooth module 1325, a GNSS module 1327 (for example, a GPS module, a Glonass module, a Beidou module, or a Galileo module), an NFC module 1328, and an RF module 1329.

The cellular module 1321 may provide a voice call, a video call, a text message service, or an Internet service through, for example, a communication network. According to an embodiment of the present disclosure, the cellular module 1321 may distinguish between and authenticate electronic devices 1301 within a communication network using a SIM (for example, the SIM card 1324). According to an embodiment of the present disclosure, the cellular module 1321 may perform at least some of the functions that the processor 1310 may provide. According to an embodiment of the present disclosure, the cellular module 1321 may include a CP.

Each of the Wi-Fi module 1323, the Bluetooth module 1325, the GNSS module 1327, and the NFC module 1328 may include a processor for processing data transmitted/received, for example, through the corresponding module. According to some embodiments of the present disclosure, at least some (two or more) of the cellular module 1321, the Wi-Fi module 1323, the Bluetooth module 1325, the GNSS module 1327, and the NFC module 1328 may be included in one integrated chip (IC) or IC package.

The RF module 1329 may transmit/receive, for example, a communication signal (for example, an RF signal). The RF module 1329 may include, for example, a transceiver, a power amp module (PAM), a frequency filter, a low noise amplifier (LNA), or an antenna. According to another embodiment of the present disclosure, at least one of the cellular module 1321, the Wi-Fi module 1323, the Bluetooth module 1325, the GNSS module 1327, or the NFC module 1328 may transmit and receive an RF signal through a separate RF module.

The SIM 1324 may include, for example, a card including a SIM and/or an embedded SIM, and may further include unique identification information (for example, an integrated circuit card identifier (ICCID)) or subscriber information (for example, international mobile subscriber identity (IMSI)).

The memory 1330 (for example, the memory 130) may include, for example, an internal memory 1332 or an external memory 1334. The internal memory 1332 may include at least one of, for example, a volatile memory (for example, a dynamic random access memory (DRAM), a static RAM (SRAM), a synchronous dynamic RAM (SDRAM), and the like) and a non-volatile memory (for example, a one-time programmable read only memory (OTPROM), a programmable ROM (PROM), an erasable and programmable ROM (EPROM), an electrically erasable and programmable ROM (EEPROM), a flash memory (for example, a NAND flash memory or a NOR flash memory), a hard driver, or a solid state drive (SSD).

The external memory 1334 may further include a flash drive, for example, a Compact Flash (CF), an SD, a Micro-SD, a Mini-SD, an eXtreme Digital (xD), a memory stick, or the like. The external memory 1334 may be functionally and/or physically connected to the electronic device 1301 through various interfaces.

The sensor module 1340 may measure, for example, a physical quantity or detect an operation state of the electronic device 1301, and may convert the measured or detected information to an electrical signal. The sensor module 1340 may include, for example, at least one of a gesture sensor 1340A, a gyro sensor 1340B, an atmospheric pressure sensor 1340C, a magnetic sensor 1340D, an acceleration sensor 1340E, a grip sensor 1340F, a proximity sensor 1340G, a color sensor 1340H (for example, red, green, and blue (RGB) sensor), a biometric sensor 1340I, a temperature/humidity sensor 1340J, an illumination sensor 1340K, and a UV sensor 1340M. Additionally or alternatively, the sensor module 1340 may include an E-nose sensor, an EMG sensor, an EEG sensor, an ECG sensor, an IR sensor, an iris sensor, and/or a fingerprint sensor. The sensor module 1340 may further include a control circuit for controlling one or more sensors included therein. In some embodiments of the present disclosure, the electronic device 1301 may further include a processor configured to control the sensor module 1340 as a part of or separately from the processor 1310, and may control the sensor module 1340 while the processor 1310 is in a sleep state.

The input device 1350 may include, for example, a touch panel 1352, a (digital) pen sensor 1354, a key 1356, or an ultrasonic input device 1358. The touch panel 1352 may use at least one of, for example, a capacitive type, a resistive type, an IR type, and an ultrasonic type. The touch panel 1352 may further include a control circuit. The touch panel 1352 may further include a tactile layer, and provide a tactile reaction to a user.

The (digital) pen sensor 1354 may include, for example, a recognition sheet which is a part of the touch panel or a separate recognition sheet. The key 1356 may include, for example, a physical button, an optical key, or a keypad. The ultrasonic input device 1358 may detect ultrasonic waves generated by an input tool through a microphone (for example, a microphone 1388) and may identify data corresponding to the detected ultrasonic waves.

The display module 1360 (for example, the display 150) may include a panel 1362, a hologram device 1364, or a projector 1366. The panel 1362 may include a component equal or similar to the display 150 of FIG. 2. The panel 1362 may be implemented to be, for example, flexible, transparent, impact-resistant, or wearable. The panel 1362 may be formed as a single module together with the touch panel 1352. The hologram device 1364 may show a three dimensional image in the air using an interference of light. The projector 1366 may display an image by projecting light onto a screen. The screen may be located, for example, in the interior of or on the exterior of the electronic device 1301. According to an embodiment of the present disclosure, the display module 1360 may further include a control circuit for controlling the panel 1362, the hologram device 1364, or the projector 1366.

The interface 1370 may include, for example, an HDMI 1372, a USB 1374, an optical interface 1376, or a D-sub-miniature (D-sub) 1378. The interface 1370 may be included in, for example, the communication interface 160 illustrated in FIG. 1. Additionally or alternatively, the interface 1370 may include, for example, a mobile high-definition link (MHL) interface, an SD card/multi-media card (MMC) interface, or an infrared data association (IrDA) standard interface.

The audio module 1380 may bilaterally convert, for example, a sound and an electrical signal. The audio module 1380 may process sound information input or output through, for example, a speaker 1382, a receiver 1384, earphones 1386, the microphone 1388, or the like.

The camera module 1391 is a device which may photograph a still image and a dynamic image. According to an embodiment of the present disclosure, the camera module 291 may include one or more image sensors (for example, a front sensor or a back sensor), a lens, an image signal processor (ISP) or a flash (for example, an LED or xenon lamp).

The power management module 1395 may manage, for example, power of the electronic device 1301. According to an embodiment of the present disclosure, the power management module 1395 may include a power management integrated circuit (PMIC), a charger integrated circuit (IC), or a battery or fuel gauge. The PMIC may have a wired and/or wireless charging scheme. Examples of the wireless charging method may include, for example, a magnetic resonance method, a magnetic induction method, an electromagnetic wave method, an acoustic method, and the like. Additional circuits (for example, a coil loop, a resonance circuit, a rectifier, etc.) for wireless charging may be further included. The battery gauge may measure, for example, a residual quantity of the battery 1396, and a voltage, a current, or a temperature while charging. The battery 1396 may include, for example, a rechargeable battery and/or a solar battery.

The indicator 1397 may indicate particular status of the electronic device 1301 or a part thereof (for example, the processor 1310), for example, a booting status, a message status, a charging status, or the like. The motor 1398 may convert an electrical signal into mechanical vibrations, and may generate a vibration or haptic effect. Although not illustrated, the electronic device 1301 may include a processing device (for example, a GPU) for supporting mobile TV. The processing unit for supporting mobile TV may process, for example, media data pursuant to a certain standard of digital multimedia broadcasting (DMB), digital video broadcasting (DVB), or media flow (MediaFlo™).

Each of the elements described in the specification may include one or more components, and the terms of the elements may be changed according to the type of the electronic device. In various embodiments of the present disclosure, the electronic device may include at least one of the elements described in the specification, and some elements may be omitted or additional elements may be further included. Some of the elements of the electronic device according to various embodiments may be coupled to form one entity, and may perform the same functions of the corresponding elements before they are coupled.

Figure 14:
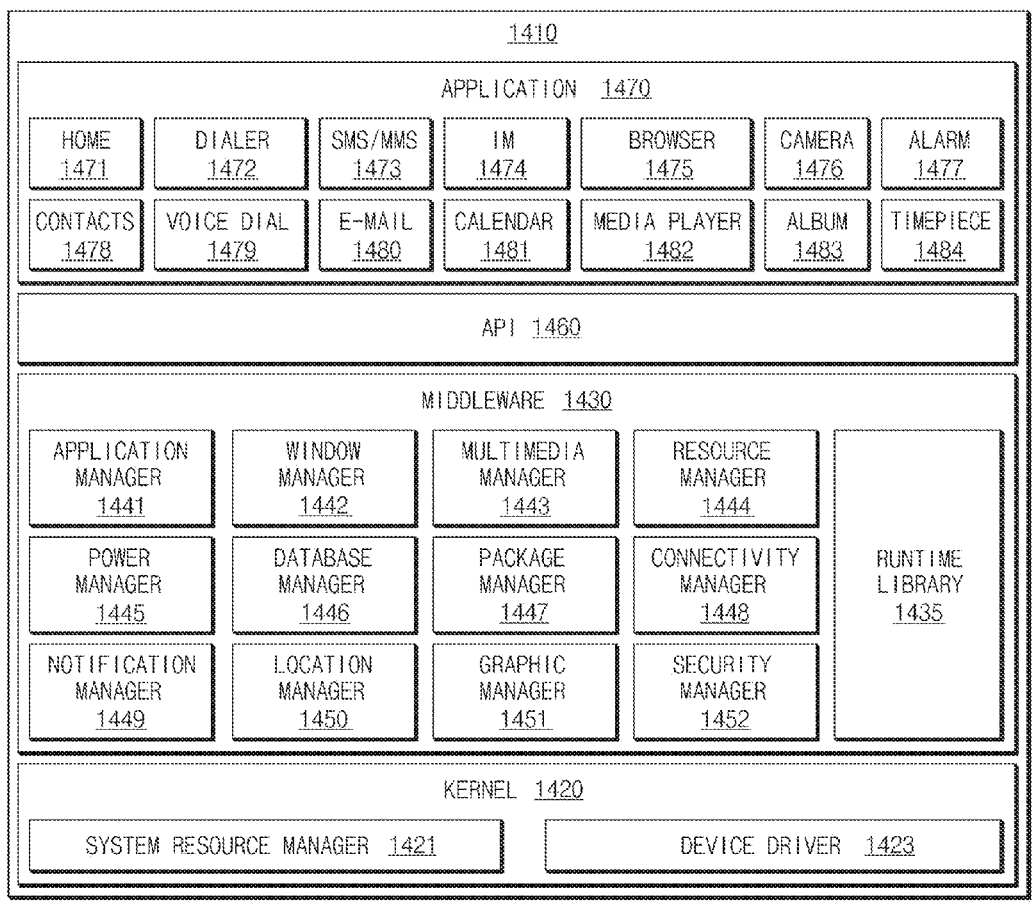
FIG. 14 is a block diagram of a program module according to various embodiments of the present disclosure.

FIG. 14 is a block diagram of a program module according to various embodiments of the present disclosure.

Referring to FIG. 14, the program module may include an OS that controls resources related to an electronic device (for example, the electronic device 101) and/or various applications that are driven on the OS. The OS may be, for example, Android, iOS, Windows, Symbian, Tizen, Bada, or the like.

A program module 1410 may include a kernel 1420, a middleware 1430, an API 1460, and/or applications 1470. At least a part of the program module 1410 may be preloaded on an electronic device or may be downloaded from external electronic devices (for example, external electronic devices 102 and 104 and a server 106).

The kernel 1420 may include, for example, a system resource manager 1421 and/or a device driver 1423. The system resource manager 1421 may control, allocate, or retrieve the system resources. According to one embodiment of the present disclosure, the system resource manager 1421 may include a process management unit, a memory management unit, or a file system management unit. The device driver 1423 may include, for example, a display driver, a camera driver, a Bluetooth driver, a shared-memory driver, a USB driver, a keypad driver, a Wi-Fi driver, an audio driver, or an inter-process communication (IPC) driver.

The middleware 1430 may provide a function required by the applications 1470 in common or provide various functions to the applications 1470 through the API 1460 so that the applications 1470 can efficiently use limited system resources of the electronic device. According to an embodiment of the present disclosure, the middleware 1430 (for example, the middleware 143) may include, for example, at least one of a runtime library 1435, an application manager 1441, a window manager 1442, a multimedia manager 1443, a resource manager 1444, a power manager 1445, a database manager 1446, a package manager 1447, a connectivity manager 1448, a notification manager 1449, a location manager 1450, a graphic manager 1451, and a security manager 1452.

The run time library 1435 may include, for example, a library module that a compiler uses in order to add new functions through a programming language while the applications 1470 are executed. The run time library 1435 may perform input/output management, memory management, or a function for an arithmetic function.

The application manager 1441, for example, may manage a lifecycle of at least one of the applications 1470. The window manager 1442 may manage a GUI resource used in a screen. The multimedia manager 1443 may detect a format required for reproducing various media files and encode or decode a media file using a codec appropriate for the corresponding format. The resource manager 1444 may manage resources, such as a source code, a memory, or a storage space, of at least one of the applications 1470.

The power manager 1445 may operate together with, for example, a basic input/output system (BIOS), so as to manage a battery or power and may provide power information required for the operation of the electronic device. The database manager 1446 may generate, search for, or change a database to be used by at least one of the applications 1470. The package manager 1447 may manage the installation or the updating of applications distributed in a package file form.

For example, the connectivity manager 1448 may manage wireless connections, such as Wi-Fi or Bluetooth. The notification manager 1449 may display or notify an event such as a received message, an appointment, a proximity notification, and the like to a user without disturbance. The location manager 1450 may manage location information of the electronic device. The graphic manager 1451 may manage graphic effects to be provided to a user and user interfaces related to the graphic effects. The security manager 1452 may provide various security functions required for system security or user authentication. According to an embodiment of the present disclosure, when the electronic device (for example, the electronic device 101) has a phone function, the middleware 1430 may further include a telephony manager for managing a voice or video communication function of the electronic device.

The middleware 1430 may include a middleware module for forming a combination of various functions of the aforementioned components. The middleware 1430 may provide modules specialized according to the type of OS in order to provide differentiated functions. In addition, some existing components may be dynamically removed from the middleware 1430, or new components may be added to the middleware 1430.

The API 1460 is, for example, a set of API programming functions, and may be provided another configuration according to an OS. For example, for each platform, one API set may be provided in a case of Android or iOS, and two or more API sets may be provided in a case of Tizen.

The application 1470 (for example, the application program 1347) may include, for example, a home 1471, a dialer 1472, an SMS/MMS 1473, an IM 1474, a browser 1475, a camera 1476, an alarm 1477, a contact 1478, a sound or voice dial 1479, an e-mail 1480, a calendar 1481, a media player 1482, an album 1483, a clock 1484, or at least one application that may provide health care (for example, measuring an exercise degree or blood glycose) or environmental information.

According to an embodiment of the present disclosure, the application 1470 may include an application (hereinafter, referred to as "an information exchange application for convenience of description) that supports exchange of information between the electronic device (for example, the electronic device 101) and external electronic device (for example, the external electronic device 102 and 104). The information exchange application may include, for example, a notification relay application for forwarding specific information to an external electronic device, or a device management application for managing an external electronic device.

For example, the notification relay application may have a function of forwarding, to external electronic devices (for example, the electronic devices 102 and 104), notification information generated from other applications of the electronic device 101 (for example, an SMS/MMS application, an e-mail application, a health care application, and an environmental information application). The notification relay application may receive notification information from, for example, an external electronic device and provide the received notification information to a user.

The device management application may, for example, manage (for example, install, delete, or update) a function for at least a part of an external electronic device (for example, the electronic device 102 or 104) communicating with the electronic device 101 (for example, activating/deactivating the external electronic device itself (or some components thereof) or adjusting the brightness (or resolution) of a display), an application operating in the external electronic device, or a service provided from the external electronic device (for example, a telephone call service or a message service).

According to an embodiment of the present disclosure, the application 1470 may include an application (for example, a health management application) designated according to an attribute of an external electronic device (for example, an electronic device 102 or 104). According to an embodiment of the present disclosure, the application 1470 may include an application that is received from an external electronic device (for example, the server 106 or the device 102 or 104). According to an embodiment of the present disclosure, the applications 1470 may include a preloaded application or a third party application that is downloaded from a server. The names of the elements of the program module 1410 according to the illustrated embodiment may vary according to the type of the OS.

According to various embodiments of the present disclosure, at least a part of the program module 1410 may be implemented by software, firmware, hardware, or two or more combinations thereof. At least a part of the program module 1410, for example, may be implemented (for example, executed) by a processor (for example, the processor 1310). At least a part of the program module 1410 may include, for example, a module, a program routine, a set of instructions, or a process for performing at least one function.

The term "module" used in the specification may mean a unit including, for example, one of hardware, software, or firmware or a combination of the two or more of them. The module may be interchangeably used, for example, with a unit, a logic, a logical block, a component, or a circuit. The module may be a minimum unit or a part of an integrally configured part. The module may be a minimum unit or a part which performs one or more functions. The module may be implemented mechanically or electromagnetically. For example, the module may include at least one of an application-specific integrated circuit (ASIC) chip, a field-programmable gate array, or a programmable-logic device, which has been known, will be developed in the future, or performs certain operations.

At least some of the devices (for example, modules or functions) or methods (for example, operations) according to various embodiments of the present disclosure may be implemented by an instruction stored in a non-transitory computer-readable storage medium, for example, in the form of a program module. When the instruction is executed by the processor (for example, the processor 120), the at least one processor may perform a function corresponding to the instruction. The computer-readable storage medium may be, for example, a memory 130.

The computer-readably storage medium may include a hard disk, a floppy disk, a magnetic medium (for example, a magnetic tape), an optical medium (for example, a compact disk read only memory (CD-ROM)), a DVD, a meneto-optical medium (for example, a floptical disk), a hardware device (for example, a read only memory (ROM), a random access memory (RAM), or a flash memory). Further, the program instructions may include high-level language codes which may be executed by a computer using an interpreter as well as machine languages created by using a compiler. The above-mentioned hardware device may be configured to be operated as one or more software module to perform operations of various embodiments of the present disclosure, and the converse is true.

The module or program module according to various embodiments of the present disclosure may include at least one of the above-mentioned element, omit some of them, or further include other elements. The module, the program module, or the operations performed by other elements according to various embodiments of the present disclosure may be performed in a sequential, parallel, iterative, or heuristic method. Further, some operations may be executed in another sequence or may be omitted, or other operations may be added. Further, the embodiments disclosed in the specification are provided to describe the technical contents or for understanding of the technical contents, and the technical scope of the present disclosure is not limited thereto. Accordingly, the scope of the present disclosure should be construed to include all changes or various embodiments based on the technical spirit of the present disclosure.

According to an embodiment of the present disclosure, because the functions of the modules that may influence biometric information are deactivated before the biometric information is measured, the measurement preciseness and reliability of the biometric information can be improved.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A method for measuring biometric information in an electronic device comprising a biometric sensor and one or more modules, the method comprising:
   receiving an event causing the biometric sensor to initiate a measurement of biometric information;
   transmitting first control information to at least one of another electronic device, a base station, or a server;
   deactivating at least one of functions of a module among the one or more modules, wherein the first control information is configured such that a communication message which is destined to the electronic device is transmitted to the other electronic device;
   measuring the biometric information;
   activating at least one of the deactivated function of the module, if the measurement of the biometric information is terminated;
   transmitting second control information to at least one of the other electronic device, the base station, or the server, if the measurement of the biometric information is terminated, wherein the second control information is configured such that the communication message which is destined to the other electronic device is transmitted to the electronic device; and
   receiving the communication message.

2. The method of claim 1, wherein the module is configured to use a current level that exceeds a predetermined value.

3. The method of claim 1, wherein the module is configured to generate a noise level that exceeds a predetermined value.

4. The method of claim 1,
   wherein the module is configured as a display module comprising a plurality of pixels, and
   wherein the deactivating of the at least one function of the module comprises deactivating at least a portion of the plurality of pixels or setting the brightness of at least a portion of the plurality of pixels to a predetermined brightness.

5. The method of claim 1,
   wherein the module is configured as a communication circuit that establishes a communication with an external device, and
   wherein the deactivating of the at least one function of the module comprises deactivating at least one function among a plurality of functions of the communication circuit.

6. The method of claim 1, wherein the module is configured to use at least one resource level that exceeds a predetermined value.

7. The method of claim 1,
   wherein activating at least one of the deactivated function of the module comprises activating at least one module that is configured to output, store, or transmit the measured biometric information.

8. The method of claim 1, wherein the biometric information comprises at least one of glucose information, heart pulsations information, electrocardiography information, electromyogram (EMG) information, oxygen saturation information, body temperature information, blood pressure information, fingerprint information, or iris information.

9. The method of claim 1, wherein the event is received by providing the electronic device with a biometric substance that is a measurement target of the biometric information.

10. The method of claim 1, wherein the event is received by connecting a measurement target of the biometric information to the electronic device.

11. The method of claim 1, wherein the event is received based on a preset time or a site where the measurement target of the biometric information is located.

12. The method of claim 1, wherein the event is received based on a speed or an acceleration of the measurement target of the biometric information.

13. The method of claim 1, wherein the server manages an instant messaging service.

14. The method of claim 1, wherein the communication message comprises an incoming call, a text, and/or multimedia.

15. An electronic device comprising:
   a biometric sensor configured to measure biometric information;
   a communication circuit;
   at least one module;
   a memory configured to store an instruction related to operations of the biometric sensor, the communication circuit, and the at least one module; and
   at least one processor electrically connected to the biometric sensor, the communication circuit, the at least one module and the memory, and configured to execute the instruction,
   wherein if an event causing the biometric sensor to initiate the measurement of the biometric information is acquired, the at least one processor is further configured to:
      transmit first control information to at least one of another electronic device, a base station, or a server through the communication circuit,
      deactivate at least one function of a specific module of the at least one module, wherein the first control information is configured such that a communication message which is destined to the electronic device is transmitted to the other electronic device,
      measure the biometric information,
      activate at least one of the deactivated function of the module, if the measurement of the biometric information is terminated,
      transmit second control information to at least one of the other electronic device, the base station, or the server, if the measurement of the biometric information is terminated, wherein the second control information is configured such that the communication message which is destined to the other electronic device is transmitted to the electronic device, and receive the communication message.

16. The electronic device of claim 15, wherein the specific module is configured to:
use a current level that exceeds a predetermined current value, or
generate a noise level that exceeds a predetermined value.

17. The electronic device of claim 15, wherein the specific module is configured to use at least one resource level that exceeds a predetermined value.

18. The electronic device of claim 15, wherein the communication message comprises an incoming call, a text, and/or multimedia.

* * * * *